(12) United States Patent
Saltzman et al.

(10) Patent No.: US 7,550,154 B2
(45) Date of Patent: Jun. 23, 2009

(54) METHODS OF TREATMENT WITH DRUG LOADED POLYMERIC MATERIALS

(75) Inventors: William Mark Saltzman, New Haven, CT (US); Tarek Fahmy, New Haven, CT (US); Peter Fong, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 11/830,212

(22) Filed: Jul. 30, 2007

(65) Prior Publication Data
US 2008/0014144 A1 Jan. 17, 2008

Related U.S. Application Data

(62) Division of application No. 11/170,803, filed on Jun. 30, 2005.

(60) Provisional application No. 60/677,991, filed on May 5, 2005, provisional application No. 60/628,778, filed on Nov. 17, 2004, provisional application No. 60/616,821, filed on Oct. 7, 2004, provisional application No. 60/585,047, filed on Jul. 1, 2004.

(51) Int. Cl.
*A61F 13/00* (2006.01)
*C07K 14/00* (2006.01)
*C07H 21/00* (2006.01)

(52) U.S. Cl. .......................... 424/484; 514/2; 530/350; 977/773

(58) Field of Classification Search ........................ None
See application file for complete search history.

(56) References Cited

U.S. PATENT DOCUMENTS

| | | | |
|---|---|---|---|
| 4,191,743 A | 3/1980 | Klemm | |
| 5,543,158 A | 8/1996 | Gref et al. | |
| 5,962,566 A | 10/1999 | Grandfils et al. | |
| 5,972,366 A | 10/1999 | Haynes | |
| 6,551,990 B2 | 4/2003 | Giachelli | |
| 6,676,963 B1 | 1/2004 | Lanza et al. | |
| 6,793,938 B2 | 9/2004 | Sankaram | |
| 2003/0235619 A1 | 12/2003 | Allen et al. | |
| 2006/0051426 A1 | 3/2006 | Golomb et al. | |

OTHER PUBLICATIONS

Anderson and Shive, et al., "Biodegradation and biocompatibility of PLA and PLGA microspheres", *Adv Drug Deliv Rev*, 28(1):5-24 (1997).
Bourges, et al., "Ocular drug delivery targeting the retina and retinal pigment epithelium using polylactide nanoparticles", *Invest Ophthalmol Vis Sci*, 44:3562-3569 (2003).
Bourla, et al., "Age-related macular degeneration: a practical approach to a challenging disease", *J. Am. Geriatr. Soc.*, 54(7):1130-5 (2006).
Brigger, et al., "Nanoparticles in cancer therapy and diagnosis", *Adv Drug Deliv Rev*, 54:631-651 (2002).
Brunner, et al., "pH and osmotic pressure inside biodegradable microspheres during erosion", *Pharm Res*, 16(6):847-53 (1999).
Cao, et al., "Production and surface modification of polylactide-based polymeric scaffolds for soft-tissue engineering", *Methods Mol Biol*, 238:87-112 (2004).
Caponetti, et al., "Microparticles of novel branched copolymers of lactic acid and amino acids: preparation and characterization", *J Pharm Sci*, 88(1):136-41 (1999).
Cho, et al., "Receptor-mediated delivery of all trans-retinoic acid to hepatocyte using poly(L-lactic acid) nanoparticles coated with galactose-carrying polystyrene", *J Control Release*, 77:7-15 (2001).
Croll, "Controllable surface modification of poly(lactic-co-glycolic acid) (PLGA) by hydrolysis or aminolysis I: physical, chemical, and theoretical aspects", *Biomacromolecules*, 5(2):463-73 (2004).
De Kozak, "Intraocular injection of tamoxifen-loaded nanoparticles: a new treatment of experimental autoimmune uveoretinitis", *Eur J Immunol*, 34: 3702-3712 (2004).
Edwards, et al., "Complement Factor H Polymorphism and Age-Related Macular Degeneration", *Science*, 308(5720):421-4 (2005).
Elamanchili, et al., "Characterization of poly(D,L-lactic-co-glycolic acid) based nanoparticulate system for enhanced delivery of antigens of dendritic cells", *Vaccine*, 22:2406-2412 (2004).
Eliaz and Szoka, "Liposome-encapsulated doxorubicin targeted to CD44: a strategy to kill CD44-overexpressing tumor cells", *Cancer Res*, 61: 2592-2601 (2001).
Eniola, et al., "Artificial polymeric cells for targeted drug delivery", *J Control Release* 87(1-3):15-22 (2003).
Evora, et al., "Relating the phagocytosis of microparticles by alveolar macrophages to surface chemistry: the effect of 1,2-dipalmitoylphosphatidylcholine", *J Control Release* 51(2-3):143-52 (1998).
Fahmy, "Increased TCR avidity after T cell activation: a mechanism for sensing low-density antigen", *Immunity*, 14:135-43 (2001).
Faraasen, et al., "Ligand-specific targeting of microspheres to phagocytes by surface modification with poly(L-lysine)-grafted poly(ethylene glycol) conjugate", *Pharm Res*, 20(2):237-46 (2003).
Garcia-Garcia, et al., "Drug-eluting stents", *Arch. Cardiol. Mex.*, 76(3):297-319 (2006) (abstract).
Guzman, et al., "Local intraluminal infusion of biodegradable polymeric nanoparticles. A novel approach for prolonged drug delivery after balloon angioplasty", *Circulation*, 94:1441-1448 (1996).
Haines, et al., "Complement factor H variant increases the risk of age-related macular degeneration", *Science*, 308(5720):419-21 (2005).

(Continued)

*Primary Examiner*—Anand U Desai
(74) *Attorney, Agent, or Firm*—Pabst Patent Group LLP

(57) ABSTRACT

Polymeric microparticles have been developed which encapsulate therapeutic compounds such as drugs, cellular materials or components, and antigens, and can have targeting ligands directly bound to the microparticle surface. Preferred applications include use in tissue engineering matrices, wound dressings, hone repair or regeneration materials, and other applications where the microparticles are retained at the site of application or implantation. Another preferred application is in the use of microparticles to deliver anti-proliferative agents to the lining of blood vessels following angioplasty, transplantation or bypass surgery to prevent or decrease restenosis, and in cancer therapy. In still another application, the microparticles are used to treat or prevent macular degeneration when administered to the eye, where agents such as complement inhibitors are administered.

19 Claims, 5 Drawing Sheets

OTHER PUBLICATIONS

Figure 1A:
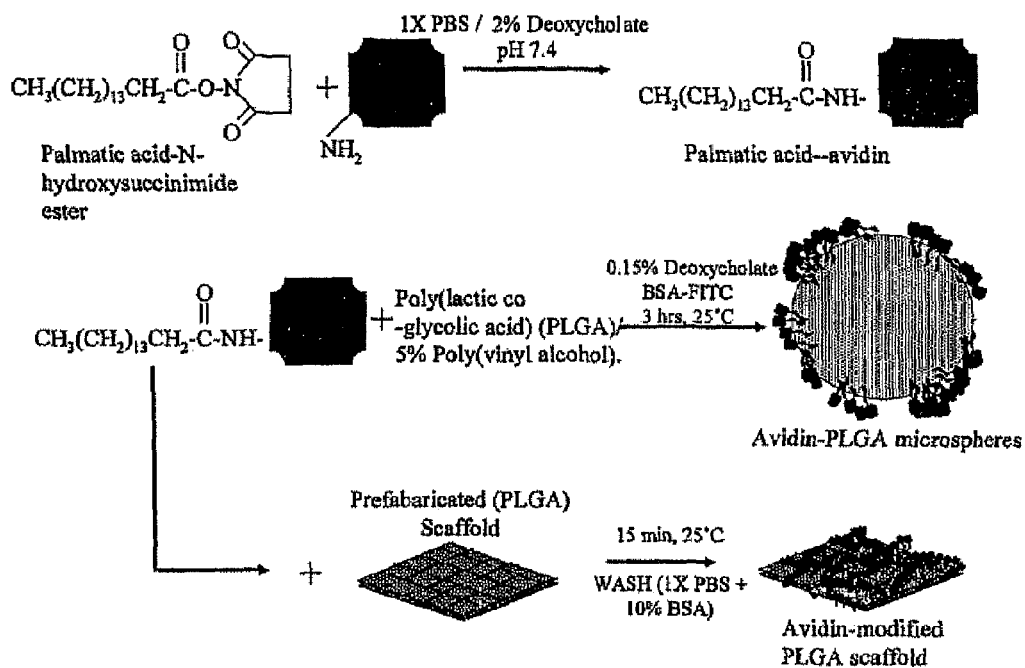
Figure 1B:
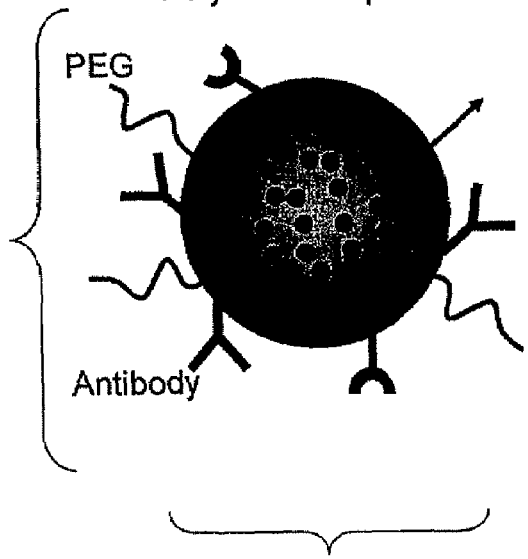

Hallahan, et al., "Integrin-mediated targeting of drug delivery to irradiated tumor blood vessels", *Cancer Cell*, 3:63-74 (2003).

Hammer, et al., "Synthetic cells-self-assembling polymer membranes and bioadhesive colloids", *Annu. Rev. Mater. Res.*, 31:387-40 (2001).

Hattori and Maitani, "Enhanced in vitro DNA transfection efficiency by novel folate-linked nanoparticles in human prostate cancer and oral cancer", *J. Control. Release*, 97(1):173-83 (2004).

Hood, et al., "Tumor regression by targeted gene delivery to the neovasculature", *Science*, 296(5577):2404-2407 (2002).

Huang, "Monoclonal antibody covalently coupled with fatty acid. A reagent for in vitro liposome targeting", *J Biol Chem*, 255(17):8015-8 (1980).

Jain, "The manufacturing techniques of various drug loaded biodegradable poly(lactide-co-glycolide) (PLGA) devices", *Biomaterials*, 21(23):2475-90 (2000).

Jansen, et al., "Encapsulation of Guest Molecules into a Dendritic Box", *Science*, 266(5188):1226-1229 (1994).

Jansen, et al., "The Dendritic Box: Shape-Selective Liberation of shell deprotection Encapsulated Guests", *Journal of the American Chemical Society*, 117:4417-4418 (1995).

Johansen, et al., "Revisiting PLA/PLGA microspheres: an analysis of their potential in parenteral vaccination", *Eur J Pharm Biopharm*, 50(1):129-46 (2000).

Keegan, et al., "Biodegradable Microspheres with Enhanced Capacity for Covalently Bound Surface Ligands" *Macromolecules*, 37:9979-84 (2004).

Keegan, et al., "Biomimetic design in microparticulate vaccines", *Biomaterials*, 24(24):4435-4443 (2003).

Klein, et al., "Complement factor H polymorphism in age-related macular degeneration", *Science*, 308(5720):385-9 (2005).

Kobayashi, "Evaluation of the in vivo biodistribution of indium-111 and yttrium-88 labeled dendrimer-1B4M-DTPA and its conjugation with anti-Tac monoclonal antibody", *Bioconjug Chem*, 10:103-11 (1999).

Kobayashi, et al., "Dendrimer-based Macromolecular MRI Contrast Agents: Characteristics and Application", *Mol Imaging*, 2:1-10 (2003).

Kompella, et al., "Subconjunctival nano- and microparticles sustain retinal delivery of budesonide, a corticosteroid capable of inhibiting VEGF expression", *Invest. Ophthalmol. Vis. Sci.*, 44(3):1192-201 (2003).

Kono, et al., *Abstracts of Papers of the American Chemical Society*, 221:U377-U377 (2001).

Labhasetwar, et al., "Arterial uptake of biodegradable nanoparticles: effect of surface modifications", *J Pharm Sci*, 87:1229-1234 (1998).

Lamprecht, et al., "Biodegradable nanoparticles for targeted drug delivery in treatment of inflammatory bowel disease", *J Pharmacol Exp Ther*, 299(2):775-81 (2001).

Langer and Folkman, "Polymers for the sustained release of proteins and other macromolecules", *Nature*, 263(5580):797-800 (1976).

Lathia, et al., "Polymeric contrast agent with targeting potential", *Ultrasonic*, 42(1-9):763-8 (2004).

Lavik, et al., "A simple synthetic route to the formation of a block copolymer of poly(lactic-co-glycolic acid) and polylysine for the fabrication of functionalized, degradable structures for biomedical applications", *J Biomed Mater Res*, 58(3):291-4 (2001).

Liu, et al., *Abstracts of Papers of the American Chemical Society*, 216:U875-U875 (1998).

Lopes De Menezes, et al., "In vitro and in vivo targeting of immunoliposomal doxorubicin to human B-cell lymphoma", *Cancer Res*, 58:3320-3330 (1998).

Luo, "Poly(ethylene glycol)-Conjugated PAMAM Dendrimer for Biocompatible, High-Efficiency DNA Delivery", *Macromolecules*, 35:3456-3462 (2002).

Luo, et al., "Controlled DNA delivery system", *Phar. Res.*, 16: 1300-1308 (1999).

Mader, et al., "Monitoring microviscosity and microacidity of the albumin microenvironment inside degrading microparticles from poly(lactide-co-glycolide) (PLG) or ABA-triblock polymers containing hydrophobic poly(lactide-co-glycolide) A blocks and hydrophilic poly(ethyleneoxide) B blocks", *Pharm Res*, 15(5):787-93 (1998).

Mainardes, et al., "Colloidal carriers for ophthalmic drug delivery", *Curr Drug Targets*, 6:363-371 (2005).

Mu, et al., "Vitamin E TPGS used as emulsifier in the solvent evaporation /extraction technique for fabrication of polymeric nanospheresfor controlled release of paclitaxel (TaxolÒ)", *J Control Release*, 80(1-3):129-44 (2002).

Mu, et al., "A novel controlled release formulation for the anticancer drug paclitaxel (Taxol®): PLGA nanoparticles containing vitamin E TPGS", *J Control Release*, 86(1):33-48 (2003).

Muller, "Surface Modification of PLGA Microspheres", *J Biomed Mater Res*, 66A(1):55-61 (2003).

Naylor, et al., "Starburst Dendrimers. 5. Molecular Shape Control", *Journal of the American Chemical Society*, 111:2339-2341 (1989).

Nunn, et al., "Complement inhibitor of C5 activation from the soft tick *Ornithodoros moubata*", *J Immunol.*, 174(4):2084-91 (2005).

Olivier, "Drug transport to brain with targeted nanoparticles", *NeuroRx*, 2:108-119 (2005).

Pan, et al., "Strategy for the treatment of myelogenous leukemia based on folate receptor β-targeted liposomal doxorubicin combined with receptor induction using all-*trans* retinoic acid", *Blood*, 100:594-602 (2002).

Panyam, "Biodegradable nanoparticles for drug and gene delivery to cells and tissue", *Adv Drug Deliv Rev*, 55(3):329-47 (2003).

Park, et al., "Anti-HER2 immunoliposomes: enhanced efficacy attributable to targeted delivery" *Clin Cancer Res*, 8:1172-1181 (2002).

Park, et al., "Integration of surface modification and 3D fabrication techniques to prepare patterned poly(L-lactide) substrate allowing regionally selective cell adhesion", *J Biomater Sci Polym Ed*, 9(2):89-110 (1998).

Park, et al., "Surface modified poly(lactide-*co*-glycolide) nanospheres for targeted bone imaging with enhanced labeling and delivery of radio isotope", *J Biomed Mater Res*, 67A(3):751-60 (2003).

Pastorino, et al., "Doxorubicin-loaded Fab' fragments of anti-disialoganglioside immunoliposomes selectively inhibit the growth and dissemination of human neuroblastoma in nude mice", *Cancer Res.*, 63(1):86-92 (2003).

Quirk, et al., "Cell-type-specific adhesion onto polymer surfaces from mixed cell populations", *Biotech. Bioeng.*, 81(5):625-628 (2003).

Schiffelers, et al., "Cancer siRNA therapy by tumor selective delivery with ligand-targeted sterically stabilized nanoparticle", *Nucleic Acids Res*, 32: e149 (2004).

Schneck, "Monitoring antigen-specific T cells using MHC-1g dimmers", *Immunol Invest*, 29:163-9 (2000).

Shenderova, et al., "The acidic microclimate in poly(lactide-co-glycolide) microspheres stabilizes camptothecins", *Pharm Res*, 16(2):241-8 (1999).

Song, et al., "Arterial uptake of biodegradable nanoparticles for intravascular local drug delivery: results with an acute dog model", *J Control Release*, 54:201-211 (1998).

Sykulev, et al., "High-affinity reactions between antigen-specific T-cell receptors and peptides associated with allogeneic and syngeneic major histocompatibility complex class 1 proteins", *Proc Natl Acad Sci U S A*, 91:11487-91 (1994).

Thomasin, et al., "Drug microencapsulation by PLA/PLGA coacervation in the light of thermodynamics. 1. Overview and theoretical considerations", *J Pharm Sci*, 87(3):259-68 (1998).

Tomalia, et al., "Starburst dendrimers: Molecular level control of size, shape, surface chemistry, topology and flexibility of atoms to macroscopic matter", *Angewandte Chemie-International Edition in English*, 29:138-175 (1990).

Visscher, et al., "Biodegradation of and tissue reaction to 50:50 poly(DL-lactide-co-glycolide) microcapsules", *J Biomed Mater Res*, 19(3):349-65 (1985).

Wan, et al., "Characterization of surface property of poly(lactide-*co*-glycolide) after plasma treatment", *Biomaterials*, 25(19):4777-83 (2004).

*Wang, et al., "Preparation and characterization of poly(lactic-co-glycolic acid) microspheres for targeted delivery of a novel anticancer agent, taxol", *Chem. Pharm. Bull.* (Tokyo), 44(10):1935-40 (1996).

Wartlick, et al., "Highly specific HER2-mediated cellular uptake of antibody-modified nanoparticles in tumor cells" *J Drug Target*, 12:461-471 (2004).

Yamaguchi and Anderson, "In vivo biocompatibility studies of medisorb © 65/35 D,L-lactide/glycolide copolymer microspheres", *J. Controlled Rel.*, 24(1-3):81-93 (1993).

Yang, et al., "Plasma-treated, collagen-anchored polylactone: Its cell affinity evaluation under shear or shear-free conditions", *J Biomed Mater Res*, 67A(4):1139-47 (2003).

Yoo, et al., "PAMAM dendrimers as delivery agents for antisense oligonucleotides", *Pharm Res*, 16:1799-804 (1999).

Zheng, et al., "Production of microspheres with surface amino groups from blends of Poly(Lactide-co-glycolide) and Poly(epsilon-CBZ-L-lysine) and use for encapsulation", *Biotechnology Progress*, 15(4):763-767 (1999).

Hattori, "Enhanced in vitro DNA transfection efficientcy by novel folate-linked nanoparticles in human prostate cancer and oral cancer" *J. Controlled. Rel.* 97:173-183(2004).

Gref, "'Stealth' corona-core nanoparticles surface modified by polyethylene glycol (PEG): influences of the corona (PEG chain length and surface density) and of the core composition on phagocytic uptake and plasma protein adsorption", *Colloids and Surfaces B: Biointerfaces*, 18(3-4): 301-313 (2000).

Gref, "Surface-engineered nanoparticles for multiple ligand coupling", *Biomaterials*, 24(24): 4529-4537 (2003).

McPhail, "Liposomes encapsulating polymeric chitosan based vesicles—a vesicle in vesicle system for drug delivery", *International Journal of Pharmaceutics*, 200(1):73-86 (2000).

Stimulation with OVA antigen

Stimulation without OVA antigen:

METHODS OF TREATMENT WITH DRUG LOADED POLYMERIC MATERIALS

CROSS-REFERENCE TO RELATED APPLICATIONS

This application claims priority as a divisional under 35 U.S.C. 119 to U.S. Ser. No. 11/170,803 filed Jun. 30, 2005, which claims priority to U.S. Ser. No. 60/677,991 filed May 5, 2005, U.S. Ser. No. 60/628,778 filed Nov. 17, 2004, U.S. Ser. No. 60/616,821 filed Oct. 7, 2004, and U.S. Ser. No. 60/585,047 filed Jul. 1, 2004. The disclosures in the applications listed above are herein incorporated in their entirety by reference.

STATEMENT REGARDING FEDERALLY SPONSORED RESEARCH

The U.S. government has certain right in this invention by virtue of grants from the National Institutes of Health (EB00487 and CA52857) to William Mark Saltzman.

FIELD OF THE INVENTION

The present invention relates to polymer microparticles for treating disorders such as restenosis, macular degeneration, cancer and transplantation.

BACKGROUND OF THE INVENTION

Biodegradable polymers have been used to deliver various therapeutic agents. The therapeutic agents typically are encapsulated within the biodegradable polymers which are formed into particles having sizes of 100 μm or less, films, sheets, disks, pellets, or implants. The biodegradable polymers are administered to a person, and the encapsulated therapeutic agent is released within the body of the patient as the polymer degrades and/or as water diffuses into the polymer to leach out the encapsulated therapeutic. Biodegradable polymers, both synthetic and natural, can release encapsulated agents over a period of days or weeks, which can have benefits in administration of drugs or other agents.

These devices have been modified to incorporate drug through such techniques as solvent encapsulation, melt encapsulation, phase separation, and other standard methods for processing of polymers. The surfaces of the polymeric devices have been modified to incorporate ligands, usually through either derivatization of the polymer before formation of the device, or after formation of the device using covalent binding to the polymer or ionic binding to charged sites on the polymer. Many of these techniques have disadvantages. Derivatization of the polymer prior to formation of the device can result in many of the ligands being encapsulated within the device, lowering the useful number of ligands available for binding or targeting. Covalent binding after formation can damage the polymers, lead to cross-reactions that decrease specificity, and is typically not highly efficient. Ionic binding is very gentle, but subject to dissociation, frequently not possible in high density, and of low specificity.

Biodegradable polymers fabricated from poly(lactic-co-glycolic acid) (PLGA) have emerged as powerful potential carriers for small and large molecules of therapeutic importance as well as scaffolds for tissue engineering applications. This importance derives from: 1) Physiologic compatibility of PLGA and its homopolymers PGA and PLA, all of which have been established as safe in humans after 30 years in various biomedical applications including drug delivery systems 2) Commercial availability of a variety of PLGA formulations for control over the rate and duration of molecules released for optimal physiological response (Visscher et al. J Biomed Mater Res 1985; 19(3):349-65; Langer R, Folkman J. Nature 1976; 263(5580):797-800; Yamaguchi. J. Controlled Rel. 1993; 24(1-3):81-93.). 3) Biodegradability of PLGA materials, which provides for sustained release of the encapsulated molecules under physiologic conditions while degrading to nontoxic, low-molecular-weight products that are readily eliminated (Shive et al. Adv Drug Deliv Rev 1997; 28(1):5-24; Johansen et al. Eur J Pharm Biopharm 2000; 50(1):129-46). 4) Control over its manufacturing into nanoscale particles (<500 nm) for potential evasion of the immune phagocytic system or fabrication into microparticles on the length scale of cells for targeted delivery of drugs or as antigen-presenting systems (Eniola et al. J Control Release 2003; 87(1-3):15-22; Jain R A. Biomaterials 2000; 21(23):2475-90). This unique combination of properties coupled with flexibility over fabrication has led to interest in modifying the PLGA surface for specific attachment to cells or organs in the body (Eniola, et al. 2003; Keegan et al., Biomaterials 2003; 24(24):4435-4443; Lamprecht et al. J Pharmacol Exp Ther 2001; 299(2):775-81; Lathia et al. Ultrasonics 2004; 42(1-9): 763-8 Park et al. J Biomed Mater Res 2003; 67A(3):751-60; Panyam Adv Drug Deliv Rev 2003; 55(3):329-47) for drug delivery and tissue engineering applications. With a functional PLGA surface, cells may be attached specifically to scaffolds enabling control over interactions that lead to formation of optimal neotissue, or encapsulated drug or antigen delivered specifically to the site of interest potentially reducing deleterious drug side effects and enhancing antigen delivery for vaccine applications.

A major difficulty associated with coupling ligands to PLGA particles has been the lack of functional chemical groups on the aliphatic polyester backbone for linking to target ligands. This severely hinders the application of traditional conjugation methods to the PLGA surface. Thus to introduce functionality into PLGA surfaces several approaches have been studied. These include, synthesis of PLGA copolymers with amine (Lavik et al J Biomed Mater Res 2001; 58(3):291-4; Caponetti et al. J Pharm Sci 1999; 88(1):136-41) or acid (Caponetti et al J Pharm Sci 1999; 88(1):136-41) end groups followed by fabrication into particles. Another approach involves the blending or adsorption of functional polymers such as polylysine (Faraasen et al. Pharm Res 2003; 20(2):237-46; Zheng et al. Biotechnology Progress 1999; 15(4):763-767) or poly(ethylene-alt-maleic acid) (PEMA) (Keegan et al. Macromolecules 2004) or PEG (Muller J Biomed Mater Res 2003; 66A(1):55-61) into PLGA and forming particles and matrices from these blends (Zheng, et al. 1999; Keegan, 2004; Park et al. J Biomater Sci Polym Ed 1998; 9(2):89-110; Croll Biomacromolecules 2004; 5(2):463-73; Cao et al. Methods Mol Biol 2004; 238:87-112). Plasma treatment of the PLGA matrix has also been proposed for the purpose of modifying its surface properties and introducing hydrophilic functional groups into the polymer (Yang et al. J Biomed Mater Res 2003; 67A(4):1139-47; Wan et al., Biomaterials 2004; 25(19):4777-83).

Targeting ligands include any molecule that recognizes and binds to target antigen or receptors over-expressed or selectively expressed by particular cells or tissue components. These may include antibodies or their fragments, peptides, glycoproteins, carbohydrates or synthetic polymers. The most widely used coupling group is poly(ethylene glycol) (PEG), because this group creates a hydrophilic surface that facilitates long circulation of the nanoparticles. This strategy has been used successfully in making 'Stealth' liposomes with affinity towards target cells. Incorporating ligands in liposomes is easily achieved by conjugation to the phospholipid head group, in most cases phosphotidylethanolamine (PE), and the strategy relies either on a preinsertion of the functionalized lipid or post insertion into a formed liposome. Functionality could also be introduced by incorporating PEG with functional endgroups for coupling to target ligands.

While these approaches have had good success in their specific applications, their general use is hindered by drawbacks such as difficulty associated with preparing the needed copolymers, limited density of functional groups and targeting effects that decrease with time due to desorption or degradation of adsorbed group as the particle or scaffold erodes. It would be most desirable to retain ligand function with control over its density on the surface for prolonged periods of time for improved drug delivery. There are also still a number of difficulties associated with preparation of co-polymers, limited density of functional groups and targeting groups with time due to degradation.

It is therefore an object of the present invention to provide a polymer delivery system which can preferentially deliver therapeutic compositions to selected cells or tissue and/or deliver high amounts of therapeutic molecules.

It is another object of the invention to provide high density, direct attachment to polymer, without harsh cross-linking or coating requirements.

SUMMARY OF THE INVENTION

Microparticles are used to deliver therapeutics, nutritional, diagnostic, or prophylactic agents in tissue engineering applications, in treatment or prevention of restenosis, in treatment or prevention of macular degeneration, and in cancer therapy. In one embodiment, the microparticles are administered with tissue engineering matrices, wound dressings, bone repair or regeneration materials, and other applications where the microparticles are retained at the site of application or implantation. Another preferred application is in the use of microparticles to deliver anti-proliferative agents to the lining of blood vessels following angioplasty, transplantation or bypass surgery to prevent or decrease restenosis, and in cancer therapy. In still another application, the microparticles are used to treat or prevent macular degeneration when administered to the eye, where agents such as complement inhibitors are administered.

Polymeric delivery devices have been developed which combine high loading/high density of molecules to be delivered with the option of targeting. As used herein, "high density" refers to microparticles having a high density of ligands or coupling agents, which is preferably in the range of 1,000 to 10,000,000, more preferably 10,000 to 1,000,000 ligands per square micron of microparticle surface area. Targeting molecules can also be attached to the surface of the polymers. Specificity is determined through the selection of the targeting molecules. The effect can also be modulated through the density and means of attachment, whether covalent or ionic, direct or via the means of linkers. Drug to be delivered can be encapsulated within the polymer and/or attached to the surface of the polymer. The same or different molecules to be delivered can be encapsulated or attached. This can provide a two phase delivery or pulsed delivery.

Figure 5A:
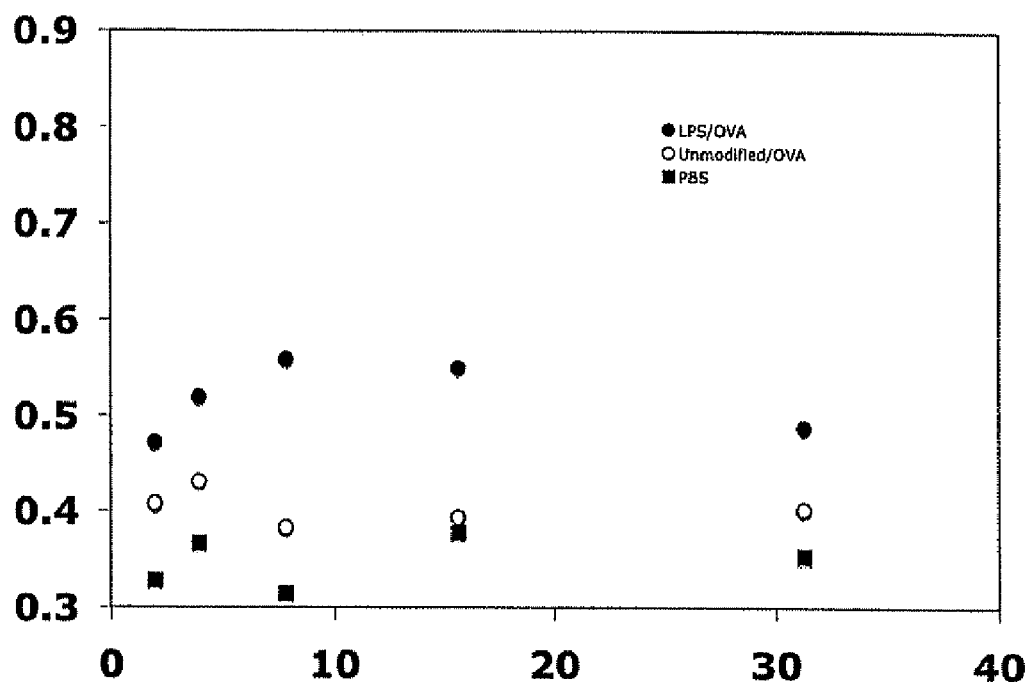
Figure 5B:
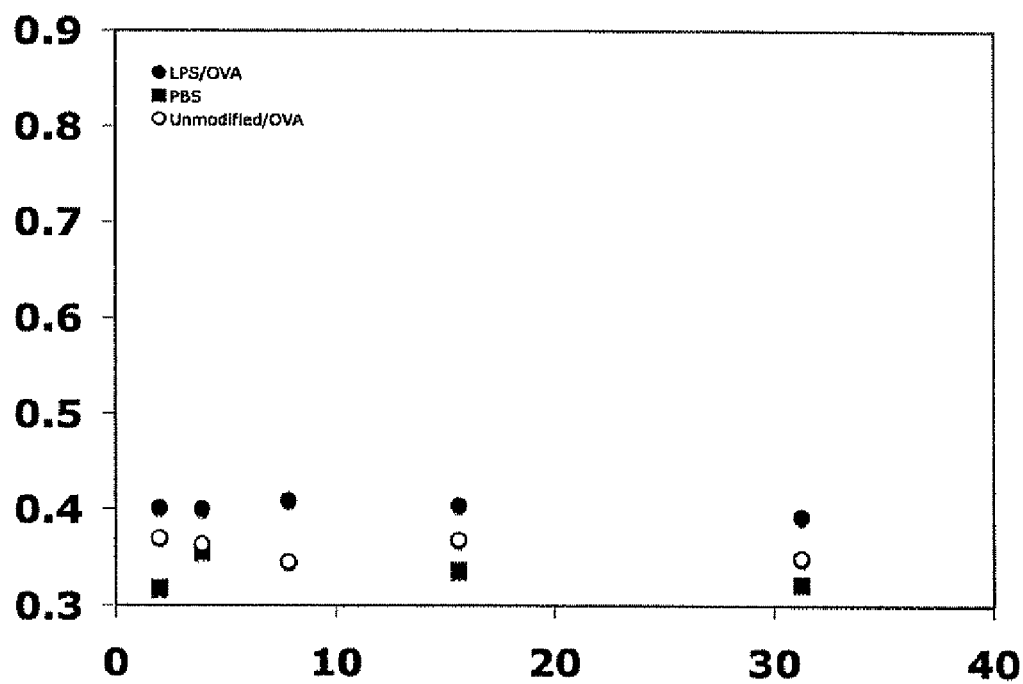

A general method for incorporating molecules into the surface of biocompatible polymers using materials with an HLB of less than 10, more preferably less than 5, such as fatty acids, has been developed. As demonstrated by the examples, avidin-fatty acid conjugates were prepared and efficiently incorporated into polylactic acid-glycolic acid ("PLGA"). In a preferred embodiment, avidin is used as an adaptor protein to facilitate the attachment of a variety of biotinylated ligands, although other attachment molecules can be used. Fatty acids preferentially associate with hydrophobic polymers, such as a PLGA matrix, rather than the external aqueous environment, facilitating a prolonged presentation of avidin over several weeks. Examples demonstrate this approach in both microparticles encapsulating a model protein, bovine serum albumin (BSA), and PLGA scaffolds fabricated by a salt leaching method. Because of its ease, generality and flexibility, this method has widespread utility in modifying the surface of polymeric materials for applications in drug delivery and tissue engineering, as well as other fields. The technology offers advantages over the prior art: high density, direct attachment to the polymer material without chemical modification of the PLGA, no harsh crosslinking reagents required, no need for a coating to provide attachment surfaces.

Targeted polymeric microparticles have also been developed which encapsulate therapeutic compounds such as drugs, cellular materials or components, and antigens, and have targeting ligands directly bound to the microparticle surface. These microparticles can be used to induce cellular immunologic responses or as therapeutics. Targeting greatly increases specificity, while not decreasing therapeutic load, such as DNA vaccines, drugs, peptides proteins or antigens. Another advantage is that more than one material can be encapsulated and/or coupled to the surface of the microparticle. This may be a therapeutic and/or targeting material. In some cases it may be advantageous to provide for an initial delivery of molecules coupled to the surface of the microparticles, with a second encapsulated therapeutic load being delivered following phagocytosis or degradation of the microparticle.

BRIEF DESCRIPTION OF THE DRAWINGS

FIG. 1A is a scheme to modify a protein with palmitic acid. NHS-palmitic acid is added to avidin at 10× molar excess and reacted in the presence of 2% deoxycholate detergent. The NHS ester reacts with avidin amine groups producing a stable amide linkage and rendering the protein hydrophobic. Both reaction and purification steps were in the presence of detergent to prevent palmitate vesicle formation. FIG. 1B is a schematic of a microparticle showing targeting molecules (antibody) and coupling agent (avidin) and linkers (polyethylene glycol, PEG) on the surface.

FIG. 2 is a graph of the degree of molecular crowding on the surface of treated particles, determined by titrating biotin-phycoerythrin ("PE") onto microparticles prepared with various concentrations of avidin-palmitic acid (micrograms). Surfaces modified with increasing amounts of the conjugate bound more of the biotinylated fluorophore, as reflected by the higher mean channel fluorescence (MCF).

FIG. 3 is a graph of the fraction of protein release over time (hours) from avidin-palmitate microparticles versus unmodified microparticles and surface modified microparticles.

FIGS. 4A and 4B are graphs of the stimulation of splenocytes from mice vaccinated by subcutaneous administration of LPS targeted microparticles encapsulating ovalbumin (closed circles) or with control microparticles: no ovalbumin (closed diamonds), no LPS targeting (open circles). FIG. 4A is stimulation of splenocytes from vaccinated mice; FIG. 4B is stimulation of vaccinated mice in the absence of ovalbumin antigen.

FIGS. 5A and 5B are graphs of the stimulation of splenocytes from mice vaccinated by oral administration of LPS targeted microparticles encapsulating ovalbunin (closed circles) or with controls: phosphate buffered saline (closed squares), no LPS targeting (open circles). FIG. 5A is stimulation of splenocytes from vaccinated mice; FIG. 5B is stimulation of vaccinated mice in the absence of ovalbumin antigen.

DETAILED DESCRIPTION OF PREFERRED EMBODIMENTS

I. Polymeric Microparticles

As used herein, microparticles generally refers to both microparticles in the range of between 0.5 and 1000 microns and nanoparticles in the range of between 50 nm to less than 0.5, preferably having a diameter that is between 1 and 20 microns or having a diameter that is between 50 and 500 nanometers, respectively. Microparticles and nanoparticles are also referred to more specifically.

The external surface of the microparticles may be modified by conjugating to the surface of the microparticle a coupling agent or ligand. As described below, in the preferred embodiment, the coupling agent is present in high density on the surface of the microparticle.

As used herein, "high density" refers to microparticles having a high density of ligands or coupling agents, which is preferably in the range of 1,000 to 10,000,000, more preferably 10,000 to 1,000,000 ligands per square micron of microparticle surface area. This can be measured by fluorescence staining of dissolved particles and calibrating this fluorescence to a known amount of free fluorescent molecules in solution.

The microparticle may be further modified by attachment of one or more different molecules to the ligands or coupling agents, such as targeting molecules, attachment molecules, and/or therapeutic, nutritional, diagnostic or prophylactic agents.

A targeting molecule is a substance which will direct the microparticle to a receptor site on a selected cell or tissue type, can serve as an attachment molecule, or serve to couple or attach another molecule. As used herein, "direct" refers to causing a molecule to preferentially attach to a selected cell or tissue type. This can be used to direct cellular materials, molecules, or drugs, as discussed below.

Improved functionality is the ability to present target for prolonged periods over the course of controlled release from the particle (weeks). Functionality is improved because target molecule remains associated with particle facilitating continuous function over the duration of controlled release.

Surface modified matrices as referred to herein present target that facilitate attachment of cells, molecules or target specific macromolecules or particles.

Control over regional modification refers to the ability to selectively modify sections of a biodegradable scaffold without modifying the whole.

By varying the polymer composition of the particle and morphology, one can effectively tune in a variety of controlled release characteristics allowing for moderate constant doses over prolonged periods of time. There have been a variety of materials used to engineer solid nanoparticles with and without surface functionality (as reviewed by Brigger et. al *Adv Drug Deliv Rev* 54, 631-651 (2002)). Perhaps the most widely used are the aliphatic polyesters, specifically the hydrophobic poly (lactic acid) (PLA), more hydrophilic poly (glycolic acid) PGA and their copolymers, poly (lactide-co-glycolide) (PLGA). The degradation rate of these polymers, and often the corresponding drug release rate, can vary from days (PGA) to months (PLA) and is easily manipulated by varying the ratio of PLA to PGA. Second, the physiologic compatibility of PLGA and its hompolymers PGA and PLA have been established for safe use in humans; these materials have a history of over 30 years in various human clinical applications including drug delivery systems. Finally, PLGA nanoparticles can be formulated in a variety of ways that improve drug pharmacokinetics and biodistribution to target tissue by either passive or active targeting.

A. Polymers

Non-biodegradable or biodegradable polymers may be used to form the microparticles. In the preferred embodiment, the microparticles are formed of a biodegradable polymer. Non-biodegradable polymers may be used for oral administration. In general, synthetic polymers are preferred, although natural polymers may be used and have equivalent or even better properties, especially some of the natural biopolymers which degrade by hydrolysis, such as some of the polyhydroxyalkanoates. Representative synthetic polymers are: poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terepthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulfate sodium salt (jointly referred to herein as "synthetic celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups and other modifications routinely made by those skilled in the art.

Examples of preferred biodegradable polymers include polymers of hydroxy acids such as lactic acid and glycolic acid, and copolymers with PEG, polyanhydrides, poly(ortho) esters, polyurethanes, poly(butyric acid), poly(valeric acid), poly(lactide-co-caprolactone), blends and copolymers thereof.

Examples of preferred natural polymers include proteins such as albumin, collagen, gelatin and prolamines, for example, zein, and polysaccharides such as alginate, cellulose derivatives and polyhydroxyalkanoates, for example, polyhydroxybutyrate. The in vivo stability of the microparticles can be adjusted during the production by using polymers such as poly(lactide-co-glycolide) copolymerized with polyethylene glycol (PEG). If PEG is exposed on the external surface, it may increase the time these materials circulate due to the hydrophilicity of PEG.

Examples of preferred non-biodegradable polymers include ethylene vinyl acetate, poly(meth)acrylic acid, polyamides, copolymers and mixtures thereof.

In a preferred embodiment, PLGA is used as the biodegradable polymer.

The microparticles are designed to release molecules to be encapsulated or attached over a period of days to weeks. Factors that affect the duration of release include pH of the surrounding medium (higher rate of release at pH 5 and below due to acid catalyzed hydrolysis of PLGA) and polymer composition. Aliphatic polyesters differ in hydrophobicity and that in turn affects the degradation rate. Specifically the hydrophobic poly (lactic acid) (PLA), more hydrophilic poly (glycolic acid) PGA and their copolymers, poly (lactide-co-glycolide) (PLGA) have various release rates. The degradation rate of these polymers, and often the corresponding drug release rate, can vary from days (PGA) to months (PLA) and is easily manipulated by varying the ratio of PLA to PGA.

Formation of Microparticles.

In addition to the preferred method described in the examples for making a high density microparticle, there may be applications where microparticles can be fabricated from different polymers using different methods.

a. Solvent Evaporation. In this method the polymer is dissolved in a volatile organic solvent, such as methylene chloride. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid microparticles. The resulting microparticles are washed with water and dried overnight in a lyophilizer. Microparticles with different sizes (0.5-1000 microns) and morphologies can be obtained by this method. This method is useful for relatively stable polymers like polyesters and polystyrene.

However, labile polymers, such as polyanhydrides, may degrade during the fabrication process due to the presence of water. For these polymers, the following two methods, which are performed in completely anhydrous organic solvents, are more useful.

b. Hot Melt Microencapsulation. In this method, the polymer is first melted and then mixed with the solid particles. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microparticles are washed by decantation with petroleum ether to give a free-flowing powder. Microparticles with sizes between 0.5 to 1000 microns are obtained with this method. The external surfaces of spheres prepared with this technique are usually smooth and dense. This procedure is used to prepare microparticles made of polyesters and polyanhydrides. However, this method is limited to polymers with molecular weights between 1,000-50,000.

c. Solvent Removal. This technique is primarily designed for polyanhydrides. In this method, the drug is dispersed or dissolved in a solution of the selected polymer in a volatile organic solvent like methylene chloride. This mixture is suspended by stirring in an organic oil (such as silicon oil) to form an emulsion. Unlike solvent evaporation, this method can be used to make microparticles from polymers with high melting points and different molecular weights. Microparticles that range between 1-300 microns can be obtained by this procedure. The external morphology of spheres produced with this technique is highly dependent on the type of polymer used.

d. Spray-Drying In this method, the polymer is dissolved in organic solvent. A known amount of the active drug is suspended (insoluble drugs) or co-dissolved (soluble drugs) in the polymer solution. The solution or the dispersion is then spray-dried. Typical process parameters for a mini-spray drier (Buchi) are as follows: polymer concentration=0.04 g/mL, inlet temperature=–24° C., outlet temperature=13-15° C., aspirator setting=15, pump setting=10 mL/minute, spray flow=600 Nl/hr, and nozzle diameter=0.5 mm. Microparticles ranging between 1-10 microns are obtained with a morphology which depends on the type of polymer used.

e. Hydrogel Microparticles. Microparticles made of gel-type polymers, such as alginate, are produced through traditional ionic gelation techniques. The polymers are first dissolved in an aqueous solution, mixed with barium sulfate or some bioactive agent, and then extruded through a microdroplet forming device, which in some instances employs a flow of nitrogen gas to break off the droplet. A slowly stirred (approximately 100-170 RPM) ionic hardening bath is positioned below the extruding device to catch the forming microdroplets. The microparticles are left to incubate in the bath for twenty to thirty minutes in order to allow sufficient time for gelation to occur. Microparticle particle size is controlled by using various size extruders or varying either the nitrogen gas or polymer solution flow rates. Chitosan microparticles can be prepared by dissolving the polymer in acidic solution and crosslinking it with tripolyphosphate. Carboxymethyl cellulose (CMC) microparticles can be prepared by dissolving the polymer in acid solution and precipitating the microparticle with lead ions. In the case of negatively charged polymers (e.g., alginate, CMC), positively charged ligands (e.g., polylysine, polyethyleneimine) of different molecular weights can be ionically attached.

B. Molecules to be Encapsulated or Attached to the Surface of the Particles

There are two principle groups of molecules to be encapsulated or attached to the polymer, either directly or via a coupling molecule: targeting molecules, attachment molecules and therapeutic, nutritional, diagnostic or prophylactic agents. These can be coupled using standard techniques. The targeting molecule or therapeutic molecule to be delivered can be coupled directly to the polymer or to a material such as a fatty acid which is incorporated into the polymer.

Functionality refers to conjugation of a ligand to the surface of the particle via a functional chemical group (carboxylic acids, aldehydes, amines, sulfhydryls and hydroxyls) present on the surface of the particle and present on the ligand to be attached. Functionality may be introduced into the particles in two ways. The first is during the preparation of the microparticles, for example during the emulsion preparation of microparticles by incorporation of stablizers with functional chemical groups. Example 1 demonstrates this type of process whereby functional amphiphilic molecules are inserted into the particles during emulsion preparation.

A second is post-particle preparation, by direct crosslinking particles and ligands with homo- or heterobifunctional crosslinkers. This second procedure may use a suitable chemistry and a class of crosslinkers (CDI, EDAC, glutaraldehydes, etc. as discussed in more detail below) or any other crosslinker that couples ligands to the particle surface via chemical modification of the particle surface after preparation. This second class also includes a process whereby amphiphilic molecules such as fatty acids, lipids or functional stabilizers may be passively adsorbed and adhered to the particle surface, thereby introducing functional end groups for tethering to ligands.

In the preferred embodiment, the surface is modified to insert amphiphilic polymers or surfactants that match the polymer phase HLB or hydrophile-lipophile balance, as demonstrated in the following example. HLBs range from 1 to 15. Surfactants with a low HLB are more lipid loving and thus tend to make a water in oil emulsion while those with a high HLB are more hydrophilic and tend to make an oil in water emulsion. Fatty acids and lipids have a low HLB below 10. After conjugation with target group (such as hydrophilic avidin), HLB increases above 10. This conjugate is used in emulsion preparation. Any amphiphilic polymer with an HLB in the range 1-10, more preferably between 1 and 6, most preferably between 1 and up to 5, can be used. This includes all lipids, fatty acids and detergents.

One useful protocol involves the "activation" of hydroxyl groups on polymer chains with the agent, carbonyldiimidazole (CDI) in aprotic solvents such as DMSO, acetone, or THF. CDI forms an imidazolyl carbamate complex with the hydroxyl group which may be displaced by binding the free amino group of a ligand such as a protein. The reaction is an N-nucleophilic substitution and results in a stable N-alkylcarbamate linkage of the ligand to the polymer. The "coupling" of the ligand to the "activated" polymer matrix is maximal in the pH range of 9-10 and normally requires at least 24 hrs. The resulting ligand-polymer complex is stable and resists hydrolysis for extended periods of time.

Another coupling method involves the use of 1-ethyl-3-(3-dimethylaminopropyl)carbodiimide (EDAC) or "water-soluble CDI" in conjunction with N-hydroxylsulfosuccinimide (sulfo NHS) to couple the exposed carboxylic groups of polymers to the free amino groups of ligands in a totally aqueous environment at the physiological pH of 7.0. Briefly, EDAC and sulfo-NHS form an activated ester with the carboxylic acid groups of the polymer which react with the amine end of a ligand to form a peptide bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-polymer complex.

By using either of these protocols it is possible to "activate" almost all polymers containing either hydroxyl or carboxyl groups in a suitable solvent system that will not dissolve the polymer matrix.

A useful coupling procedure for attaching ligands with free hydroxyl and carboxyl groups to polymers involves the use of the cross-linking agent, divinylsulfone. This method would be useful for attaching sugars or other hydroxylic compounds with bioadhesive properties to hydroxylic matrices. Briefly, the activation involves the reaction of divinylsulfone to the hydroxyl groups of the polymer, forming the vinylsulfonyl ethyl ether of the polymer. The vinyl groups will couple to alcohols, phenols and even amines. Activation and coupling take place at pH 11. The linkage is stable in the pH range from 1-8 and is suitable for transit through the intestine.

Any suitable coupling method known to those skilled in the art for the coupling of ligands and polymers with double bonds, including the use of UV crosslinking, may be used for attachment of molecules to the polymer.

Coupling is preferably by covalent binding but it may also be indirect, for example, through a linker bound to the polymer or through an interaction between two molecules such as strepavidin and biotin. It may also be by electrostatic attraction by dip-coating.

The molecules to be delivered can also be encapsulated into the polymer using double emulsion solvent evaporation techniques, such as that described by Luo et al., Controlled DNA delivery system, Phar. Res., 16: 1300-1308 (1999).

i. Molecules to be Delivered

Agents to be delivered include therapeutic, nutritional, diagnostic, and prophylactic compounds. Proteins, peptides, carbohydrates, polysaccharides, nucleic acid molecules, and organic molecules, as well as diagnostic agents, can be delivered. The preferred materials to be incorporated are drugs and imaging agents. Therapeutic agents include antibiotics, antivirals (especially protease inhibitors alone or in combination with nucleosides for treatment of HIV or Hepatitis B or C), anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs, antisense, aptamers, ribozymes, external guide sequences for ribonuclease P, and triplex forming agents).

Particularly preferred drugs to be delivered include anti-angiogenic agents, antiproliferative and chemotherapeutic agents such as rampamycin. Incorporated into microparticles, these agents may be used to treat cancer or eye diseases, or prevent restenosis following administration into the blood vessels. Exemplary diagnostic materials include paramagnetic molecules, fluorescent compounds, magnetic molecules, and radionuclides.

Alternatively, the biodegradable polymers may encapsulate cellular materials, such as for example, cellular materials to be delivered to antigen presenting cells as described below to induce immunological responses.

Peptide, protein, and DNA based vaccines may be used to induce immunity to various diseases or conditions. For example, sexually transmitted diseases and unwanted pregnancy are world-wide problems affecting the health and welfare of women. Effective vaccines to induce specific immunity within the female genital tract could greatly reduce the risk of STDs, while vaccines that provoke anti-sperm antibodies would function as immunocontraceptives. Extensive studies have demonstrated that vaccination at a distal site—orally, nasally, or rectally, for example—can induce mucosal immunity within the female genital tract. Of these options, oral administration has gained the most interest because of its potential for patient compliance, easy administration and suitability for widespread use. Oral vaccination with proteins is possible, but is usually inefficient or requires very high doses. Oral vaccination with DNA, while potentially effective at lower doses, has been ineffective in most cases because 'naked DNA' is susceptible to both the stomach acidity and digestive enzymes in the gastrointestinal tract Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Biodegradable polymer particles offer several advantages for use as DNA delivery vehicles for DNA based vaccines. The polymer particles can be biodegradable and biocompatible, and they have been used successfully in past therapeutic applications to induce mucosal or humoral immune responses. Polymer biodegradation products are typically formed at a relatively slow rate, are biologically compatible, and result in metabolizable moieties. Biodegradable polymer particles can be manufactured at sizes ranging from diameters of several microns (microparticles) to particles having diameters of less than one micron (nanoparticles).

Dendritic cells (DCs) are recognized to be powerful antigen presenting cells for inducing cellular immunologic responses in humans. DCs prime both CD8+ cytotoxic T-cell (CTL) and CD4+ T-helper (Th1) responses. DCs are capable of capturing and processing antigens, and migrating to the regional lymph nodes to present the captured antigens and induce T-cell responses. Immature DCs can internalize and process cellular materials, such as DNA encoding antigens, and induce cellular immunologic responses to disease effectors.

As used herein, the term "disease effector agents" refers to agents that are central to the causation of a disease state in a subject. In certain circumstances, these disease effector agents are disease-causing cells which may be circulating in the bloodstream, thereby making them readily accessible to extracorporeal manipulations and treatments. Examples of such disease-causing cells include malignant T-cells, malignant B cells, T-cells and B cells which mediate an autoimmune response, and virally or bacterially infected white blood cells which express on their surface viral or bacterial peptides or proteins. Exemplary disease categories giving rise to disease-causing cells include leukemia, lymphoma, autoimmune disease, graft versus host disease, and tissue rejection. Disease associated antigens which mediate these disease states and which are derived from disease-causing cells include peptides that bind to a MHC Class I site, a MHC Class II site, or to a heat shock protein which is involved in transporting peptides to and from MHC sites (i.e., a chaperone). Disease associated antigens also include viral or bacterial peptides which are expressed on the surface of infected white blood cells, usually in association with an MHC Class I or Class II molecule.

Other disease-causing cells include those isolated from surgically excised specimens from solid tumors, such as lung, colon, brain, kidney or skin cancers. These cells can be manipulated extracorporeally in analogous fashion to blood leukocytes, after they are brought into suspension or propagated in tissue culture. Alternatively, in some instances, it has been shown that the circulating blood of patients with solid tumors can contain malignant cells that have broken off from the tumors and entered the circulation. These circulating tumor cells can provide an easily accessible source of cancer cells which may be rendered apoptotic and presented to the antigen presenting cells.

In addition to disease-causing cells, disease effector agents include microbes such as bacteria, fungi, yeast, viruses which express or encode disease-associated antigens, and prions.

The disease effector agents are presented to the antigen presenting cells using biodegradable polymer microparticles as delivery vehicles. The loaded microparticles are exposed to immature antigen presenting cells, which internalize the microparticles and process the material within the microparticles. The microparticles may be administered to the patient and the interaction between the microparticles and the antigen presenting cells may occur in vivo. In a preferred embodiment, the microparticles are placed in an incubation bag with the immature antigen presenting cells, and the microparticles are phagocytosed by the antigen presenting cells during the incubation period. The resulting antigen presenting cells are then administered to the patient to induce an immune response to the disease causing agent.

ii. Targeting Molecules

Targeting molecules can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques. Table 1 is a list of ligand-targeted nanoparticulate systems providing examples of useful ligands and their targets. Examples of molecules targeting extracellular matrix ("ECM") include glycosaminoglycan ("GAG") and collagen. In one embodiment, the external surface of polymer microparticles may be modified to enhance the ability of the microparticles to interact with selected cells or tissue. The method of example 1 wherein a fatty acid conjugate is inserted into the microparticle is preferred. However, in another embodiment, the outer surface of a polymer microparticle having a carboxy terminus may be linked to PAMPs that have a free amine terminus. The PAMP targets Toll-like Receptors (TLRs) on the surface of the cells or tissue, or signals the cells or tissue internally, thereby potentially increasing uptake. PAMPs conjugated to the particle surface or co-encapsulated may include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

TABLE 1

Selected list of ligand-targeted nanoparticulate systems evaluated for in vitro or in vivo therapeutics delivery

| Ligand | Drug | System | Target Cells | Evaluation |
|---|---|---|---|---|
| Nucleic acids | | | | |
| Aptamers[a] | | PLA | Prostate Epithelial cells | In vitro |
| ECM Proteins | | | | |
| Integrin[b] | Raf genes | Liposomes | Melanoma cells | In vivo |
| RGD peptides[c] | siRNA | poly(ethylene Imine) | tumor vasculature | In vivo |

TABLE 1-continued

Selected list of ligand-targeted nanoparticulate systems evaluated for in vitro or in vivo therapeutics delivery

| Ligand | Drug | System | Target Cells | Evaluation |
|---|---|---|---|---|
| Fibrinogen[d] | radioisotopes | Albumin | tumor vasculature | In vivo |
| | | Lipids | | |
| MP Lipid A[e] | | PLGA | Dendritic cells | In vitro |
| | | Carbohydrates | | |
| Galactose[f] | retinoic acid | PLA | Hepatocytes | In vitro |
| Hyaluronic acid[g] | Doxorubicin | Liposomes | CD44+ melanoma cells | In vitro |
| Peptidomimetics[h] | Various | mPEG/PLGA | Brain cells | Various |
| | | Antibodies to: | | |
| HER2 receptor[i] | | gelatin/HAS | HER2 cells | In vitro |
| HER2 receptor[j] | Doxorubicin | Liposomes | HER2 cells | In vivo |
| CD19[k] | Doxorubicin | Liposomes | B cell lymphoma | In vivo |
| | | Vitamins | | |
| Folate[l] | Doxorubicin | Liposomes | Leukemia cells | In vivo |

[a]Park, J. W. et al. Clin Cancer Res 8, 1172-1181 (2002).
[b]Hood, J. D. et al. Science 296, 2404-2407 (2002).
[c]Schiffelers, R. M. et al. Nucleic Acids Res 32, e149 (2004).
[d]Hallahan, D. et al. Cancer Cell 3, 63-74 (2003).
[e]Elamanchili, et al. Vaccine 22, 2406-2412 (2004).
[f]Cho, C. S. et al. J Control Release 77, 7-15 (2001).
[g]Eliaz, R. E. & Szoka, F. C., Jr. Cancer Res 61, 2592-2601 (2001).
[h]Olivier, J. C. Neurorx 2, 108-119 (2005).
[i]Wartlick, H. et al. J Drug Target 12, 461-471 (2004).
[j]Park, J. W. et al. Clin Cancer Res 8, 1172-1181 (2002)
[k]Lopes de Menezes, et al. Cancer Res 58, 3320-3330 (1998).
[l]Pan, X. Q. et al. Blood 100, 594-602 (2002).

In another embodiment, the outer surface of the microparticle may be treated using a mannose amine, thereby mannosylating the outer surface of the microparticle. This treatment may cause the microparticle to bind to the target cell or tissue at a mannose receptor on the antigen presenting cell surface. Alternatively, surface conjugation with an immunoglobulin molecule containing an Fc portion (targeting Fc receptor), heat shock protein moiety (HSP receptor), phosphatidylserine (scavenger receptors), and lipopolysaccharide (LPS) are additional receptor targets on cells or tissue.

Lectins that can be covalently attached to microparticles to render them target specific to the mucin and mucosal cell layer include lectins isolated from *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limax fluvus, Homarus americanus, Cancer antennarius*, and *Lotus tetragonolobus*.

The attachment of any positively charged ligand, such as polyethyleneimine or polylysine, to any microparticle may improve bioadhesion due to the electrostatic attraction of the cationic groups coating the beads to the net negative charge of the mucus. The mucopolysaccharides and mucoproteins of the mucin layer, especially the sialic acid residues, are responsible for the negative charge coating. Any ligand with a high binding affinity for mucin could also be covalently linked to most microparticles with the appropriate chemistry, such as the fatty acid conjugates of example 1 or CDI, and be expected to influence the binding of microparticles to the gut. For example, polyclonal antibodies raised against components of mucin or else intact mucin, when covalently coupled to microparticles, would provide for increased bioadhesion. Similarly, antibodies directed against specific cell surface receptors exposed on the lumenal surface of the intestinal tract would increase the residence time of beads, when coupled to microparticles using the appropriate chemistry. The ligand affinity need not be based only on electrostatic charge, but other useful physical parameters such as solubility in mucin or else specific affinity to carbohydrate groups.

The covalent attachment of any of the natural components of mucin in either pure or partially purified form to the microparticles would decrease the surface tension of the bead-gut interface and increase the solubility of the bead in the mucin layer. The list of useful ligands would include but not be limited to the following: sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, fucose, any of the partially purified fractions prepared by chemical treatment of naturally occurring mucin, e.g., mucoproteins, mucopolysaccharides and mucopolysaccharide-protein complexes, and antibodies immunoreactive against proteins or sugar structure on the mucosal surface.

The attachment of polyamino acids containing extra pendant carboxylic acid side groups, e.g., polyaspartic acid and polyglutamic acid, should also provide a useful means of increasing bioadhesiveness. Using polyamino acids in the 15,000 to 50,000 kDa molecular weight range would yield chains of 120 to 425 amino acid residues attached to the surface of the microparticles. The polyamino chains would increase bioadhesion by means of chain entanglement in mucin strands as well as by increased carboxylic charge.

Surface Modification with Liposomes

Microparticles can be further modified by encapsulation within liposomes.

II. Applications

A. Drug Delivery

The submicron size of nanoparticulates offers distinct advantages over larger systems: First, the small size enables them to extravasate through blood vessels and tissue. This is especially important for tumor vessels, which are often dilated and fenestrated with an average pore size less than a micron, compared to normal tissue. Second, solid nanoparticles made from biodegradable polymers and encapsulating drug are ideal for sustained intracellular drug delivery, especially for drugs whose targets are cytoplasmic. An example of this application with dexamethasone-loaded nanoparticles locally delivered to vascular smooth muscle cells showed greater and sustained anti-proliferative activity compared to free drug, indicating more efficient interaction of the drug with cytoplasmic glucorticoid receptors. The dosage loading varies depending on the nature of encapsulant. Up to 80% of initial total amount of agent to be incorporated can be encapsulated in the microparticles.

The microparticles are useful in drug delivery (as used herein "drug" includes therapeutic, nutritional, diagnostic and prophylactic agents), whether injected intravenously, subcutaneously, or intramuscularly, administered to the nasal or pulmonary system, administered to a mucosal surface (vaginal, rectal, buccal, sublingual), or encapsulated for oral delivery. As noted above, the term "microparticle" includes "nanoparticles" unless otherwise stated. The dosage is determined using standard techniques based on the drug to be delivered and the method and form of administration. The microparticles may be administered as a dry powder, as an aqueous suspension (in water, saline, buffered saline, etc), in a hydrogel, organogel, or liposome, in capsules, tablets, troches, or other standard pharmaceutical excipient.

In a preferred embodiment for delivery to a mucosal surface, the microparticles are modified to include ligands for mucosal proteins or extracellular matrix as described above.

i. Restenosis and Transplantation

Percutaneous transluminal coronary angioplasty (PTCA) is a procedure in which a small balloon-tipped catheter is passed down a narrowed coronary artery and then expanded to re-open the artery. It is currently performed in approximately 250,000-300,000 patients each year. The major advantage of this therapy is that patients in which the procedure is successful need not undergo the more invasive surgical procedure of coronary artery bypass graft. A major difficulty with PTCA is the problem of post-angioplasty closure of the vessel, both immediately after PTCA (acute reocclusion) and in the long term (restenosis).

The mechanism of acute reocclusion appears to involve several factors and may result from vascular recoil with resultant closure of the artery and/or deposition of blood platelets along the damaged length of the newly opened blood vessel followed by formation of a fibrin/red blood cell thrombus. Restenosis (chronic reclosure) after angioplasty is a more gradual process than acute reocclusion: 30% of patients with subtotal lesions and 50% of patients with chronic total lesions will go on to restenosis after angioplasty. Although the exact hormonal and cellular processes promoting restenosis are still being determined, it is currently understood that the process of PTCA, besides opening the artherosclerotically obstructed artery, also injures resident coronary arterial smooth muscle cells (SMC). In response to this injury, adhering platelets, infiltrating macrophages, leukocytes, or the smooth muscle cells (SMC) themselves release cell derived growth factors with subsequent proliferation and migration of medial SMC through the internal elastic lamina to the area of the vessel intima. Further proliferation and hyperplasia of intimal SMC and, most significantly, production of large amounts of extracellular matrix over a period of 3-6 months, results in the filling in and narrowing of the vascular space sufficient to significantly obstruct coronary blood flow.

The treatment of restenosis requires additional, generally more invasive, procedures, including coronary artery bypass graft (CABG) in severe cases. Consequently, methods for preventing restenosis, or treating incipient forms, are being aggressively pursued. One possible method for preventing restenosis is the administration of anti-inflammatory compounds that block local invasion/activation of monocytes thus preventing the secretion of growth factors that may trigger SMC proliferation and migration. Other potentially anti-restenotic compounds include antiproliferative agents that can inhibit SMC proliferation, such as rapamycin and paclitaxel. Rapamycin is generally considered an immunosuppressant best known as an organ transplant rejection inhibitor. However, rapamycin is also used to treat severe yeast infections and certain forms of cancer. Paclitaxel, known by its trade name Taxol®, is used to treat a variety of cancers, most notably breast cancer.

However, anti-inflammatory and antiproliferative compounds can be toxic when administered systemically in anti-restenotic-effective amounts. Furthermore, the exact cellular functions that must be inhibited and the duration of inhibition needed to achieve prolonged vascular patency (greater than six months) are not presently known. Moreover, it is believed that each drug may require its own treatment duration and delivery rate. Therefore, in situ, or site-specific drug delivery using anti-restenotic coated stents has become the focus of intense clinical investigation. Recent human clinical studies on stent-based delivery of rapamycin and paclitaxel have demonstrated excellent short-term anti-restenotic effectiveness. Stents, however, have drawbacks due to the very high mechanical stresses, the need for an elaborate procedure for stent placement, and manufacturing concerns associated with expansion and contraction.

One of the most promising applications for targeted drug delivery using nanoparticles is in local application using interventional procedures such as catheters. Potential applications have focused on intra-arterial drug delivery to localize therapeutic agents in the arterial wall to inhibit restenosis (Labhasetwar, et al. *J Pharm Sci* 87, 1229-1234 (1998); Song, et al. *J Control Release* 54, 201-211 (1998)). Restenosis is the re-obstruction of an artery following interventional procedures such as balloon angioplasty or stenting as described above. Drug loaded nanoparticles are delivered to the arterial lumen via catheters and retained by virtue of their size, or they may be actively targeted to the arterial wall by non-specific interactions such as charged particles or particles that target the extracellular matrix. Surface-modified nanoparticles, engineered to display an overall positive charge facilitated adhesion to the negatively charged arterial wall and showed a 7 to 10-fold greater arterial localized drug levels compared to the unmodified nano-particles in different models. This was demonstrated to have efficacy in preventing coronary artery restenosis in dogs and pigs (Labhasetwar, et al. *J Pharm Sci* 87, 1229-1234 (1998)). Nanoparticles loaded with dexamethasone and passively retained in arteries showed reduction in neointimal formation after vascular injury (Guzman, et al. *Circulation* 94, 1441-1448 (1996)).

The microparticles (and/or nanoparticles) can be used in these procedures to prevent or reduce restenosis. Microparticles can be delivered at the time of bypass surgery, transplant surgery or angioplasty to prevent or minimize restenosis. The microparticles can be administered directly to the endothelial surface as a powder or suspension, during or after the angioplasty, or coated onto or as a component of a stent which is applied at the time of treatment. The microparticles can also be administered in conjunction with coronary artery bypass surgery. In this application, particles are prepared with appropriate agents such as anti-inflammatories or anti-proliferatives. These particles are made to adhere to the outside of the vessel graft by addition of adhesive ligands as described above. A similar approach can be used to add anti-inflammatory or immunosuppressant loaded particles to any transplanted organs or tissues.

In this embodiment, the drug to be delivered is preferably an anti-proliferative such as taxol, rapamycin, sirulimus, or other antibiotic inhibiting proliferation of smooth muscle cells, alone or in combination with an anti-inflammatory, such as the steroidal anti-inflammatory dexamethasone. The drug is encapsulated within and optionally also bound to the microparticles. The preferred size of the microparticles is less than one micron, more preferably approximately 100 nm in diameter. The polymer is preferably a polymer such as poly (lactic acid-co-glycolic acid) or polyhydroxyalkanoate which degrades over a period of weeks to months. Preferably the microparticles have a high density of an adhesive molecule on the surface such as one that adds charge for electrostatic adhesion, or one that binds to extracellular matrix or cellular material, or otherwise inert molecules such as an antibody to extracellular matrix component. Biotinylated particles have a higher level of adhesion to the tissue.

ii. Treatment of Tumors

Passive delivery may also be targeted to tumors. Aggressive tumors inherently develop leaky vasculature with 100 to 800 nm pores due to rapid formation of vessels that must serve the fast-growing tumor. This defect in vasculature coupled with poor lymphatic drainage serves to enhance the permeation and retention of nanoparticles within the tumor region. This is often called the EPR effect. This phenomenon is a form of 'passive targeting'. The basis for increased tumor specificity is the differential accumulation of drug-loaded nanoparticles in tumor tissue versus normal cells, which results from particle size rather than binding. Normal tissues contain capillaries with tight junctions that are less permeable to nanosized particles. Passive targeting can therefore result in increases in drug concentrations in solid tumors of several-fold relative to those obtained with free drugs.

Passive delivery may also be directed to lymphoid organs of the mammalian immune system, such as lymphatic vessels and spleen. These organs are finely structured and specialized in eliminating invaders that have gained entry to tissue fluids. Nanoparticles may easily penetrate into lymphatic vessels taking advantage of the thin walls and fenestrated architecture of lymphatic microvessels. Passive targeting to the spleen is via a process of filtration. Indeed the spleen filters the blood of foreign particles larger than 200 nm. This function facilitates splenic targeting with nanoparticles encapsulating drug for effective treatments against several hematological diseases.

Both liposomal and solid nanoparticles formulations have received clinical approval for delivery of anticancer drugs. Liposomal formulations include those of doxorubicin (Doxil1/Caelyx1 and Myocet1) and daunorubicin (Daunosome1). The mechanism of drug release from liposomes is not clear, but is thought to depend on diffusion of the drug from the carrier into the tumor interstitium. This is followed by subsequent uptake of the released drug by tumor cells. The mechanism of release is still poorly understood, which hinders advanced applications involving the addition of active ligands for cellular targeting in vivo. Recently, the FDA approved Abraxane, an albumin-bound paclitaxel nanoparticles formulation as an injectable suspension for the treatment of metastatic breast cancer. In addition, other solid nanoparticle-based cancer therapies have been approved for clinical trials, for example a Phase 1 clinical trial has been approved that will evaluate the safety of hepatic arterial infusion of REXIN-GTM (a targeted nanoparticle vector system with a proprietary mutant cell-cycle control gene, i.e. anticancer gene) as an intervention for colorectal cancer.

The particles described herein should be efficacious in the treatment of tumors, especially those where targeting is beneficial and delivery of high doses of chemotherapeutic desirable. An important feature of targeted particle delivery is the ability to simultaneously carry a high density of drug while displaying ligands on the surface of the particle. It is well known that other drug carrier systems, such as immunotoxins or drug-immunoconjugate, which are made by tethering drug molecules to antibodies or synthetic polymers, usually deliver less than 10 drug molecules per carrier to target cells. Targeted high density nanoparticles on the other hand can deliver thousands of drug molecules on the surface, and millions of molecules in their interior.

One important target is E-selectin, which is involved in the arrest of circulating immune system cells and is differentially upregulated with inflammatory and immune processes and should be useful to enhance delivery of therapeutic agents to the vasculature including tumor blood vessels through selective targeting. A second important class of targets is receptors involved in the uptake of vitamin B12, folic acid, biotin and thiamine. These are differentially overexpressed on the surface of cancer cells creating a possible target for several types of cancer, including ovarian, breast, lung, renal and colorectal cancers. One of the most promising strategies for enhancing active immunotherapy and inducing potent vaccination is targeting of antigen-loaded nanoparticles to antigen-presenting cells such as dendritic cells (DCs). Nanoparticles incorporating toll-like receptors (TLRs) in biodegradable PLGA have shown efficient delivery of antigen to DC and potent activation of the T cell immune response.

The overall strength of nanoparticles binding to a target is a function of both affinity of the ligand-target interaction and the number of targeting ligands presented on the particle surface. Nanoparticles produced by the present techniques have many thousands of ligands on their surface. This is a particularly useful feature for ligands that in their monomer form have a weak affinity to their target receptors, such as single chain variable fragments (scFv), which in most cases must be reengineered into multimers to increase their avidity of interaction to target cells or peptide/Major histocompatability complex (peptide/MHC), which have weak affinity to target T cell receptors. For example, multivalency increases the avidity of interaction of peptide/MHC to the T cell up to 100 fold facilitating enhanced interactions and effective drug delivery to target antigen-specific T cells.

iii. Macular Degeneration

Macular degeneration (MD) is a chronic eye disease that occurs when tissue in the macula, the part of the retina that is responsible for central vision, deteriorates. Degeneration of the macula causes blurred central vision or a blind spot in the center of your visual field. Macular degeneration occurs most often in people over 60 years old, in which case it is called Age-Related Macular Degeneration (ARMD) or (AMD). AMD is the leading cause of blindness in the United States and many European countries. About 85-90% of AMD cases are the dry, atrophic, or nonexudative form, in which yellowish spots of fatty deposits called drusen appear on the macula. The remaining AMD cases are the wet form, so called because of leakage into the retina from newly forming blood vessels in the choroid, a part of the eye behind the retina. Normally, blood vessels in the choroid bring nutrients to and carry waste products away from the retina. Sometimes the fine blood vessels in the choroid underlying the macula begin to proliferate, a process called choroidal neovascularization (CNV). When those blood vessels proliferate, they leak, causing damage to cells in the macula often leading to the death of such cells. The neovascular "wet" form of AMD is responsible for most (90%) of the severe loss of vision. There is no cure available for "wet" or "dry" AMD.

The exact causes of AMD are not known, however, contributing factors have been identified. Factors that contribute to AMD include reactive oxidants which cause oxidative damage to the cell s of the retina and the macula, high serum low density cholesterol lipoprotein (LDL) concentration, and neovascularization of the choroid tissue underlying the photoreceptor cells in the macula.

Treatments for wet AMD include photocoagulation therapy, photodynamic therapy, and transpupillary thermotherapy. A treatment with transpupillary thermotherapy (TTT) photocoagulation is a method of delivering heat to the back of the patient's eye using an 810 nm infrared laser, which results in closure of choroidal vessels. AMD treatment with photocoagulation therapy involves a laser aimed at leakage points of neovascularizations behind the retina to prevent leakage of the blood vessel. Photodynamic therapy (PDT) employs the photoreactivity of a molecule of the porphyrin type, called verteporphin or Visudyne, which can be performed on leaky subfoveal or juxtafoveal neovascularizations. Macugen is an FDA approved drug that inhibits abnormal blood vessel growth by attacking a protein that causes abnormal blood vessel growth.

Other potential treatments for "wet" AMD that are under investigation include angiogenesis inhibitors, such as anti-VEGF antibody, and anti-VEGF aptamer (NX-1838), integrin antagonists to inhibit angiogenesis has also been proposed, and PKC412, an inhibitor of protein kinase C. Cytochalasin E (Cyto E), a natural product of a fungal species that inhibits the growth of new blood vessels is also being investigated to determine if it will block growth of abnormal blood vessels in humans. The role of hormone replacement therapy is being investigated for treatment of AMD in women.

There are no treatments available to reverse "dry" AMD. Treatments shown to inhibit progression of AMD include supplements containing antioxidants. The use of a gentle "sub-threshold" diode laser treatment that minimizes damage to the retina is being investigated for treatment of "dry" AMD. Another potential treatment for AMD includes rheopheresis, which is a form of therapeutic blood filtration that removes "vascular risk factor" including LDL cholesterol, fibrinogen, and lipoprotein A. Rheopheresis has not yet been FDA-approved, but is available in Canada and Europe. Other treatments for AMD under investigation include culturing and transplantation of cells of the Retinal Pigment Epithelium (RPE), metalloproteinase modulators, inhibitors of A2E, a vitamin A derivative, which accumulates in the human eye with age, and carotenoids, zeaxanthin and lutein.

There have been a number of recent studies indicating that macular degeneration is caused by, or associated with, a defect in complement factor H (Haines, et al. Science. 2005 Apr. 15; 308(5720):419-21; Edwards, et al. Science. 2005 Apr. 15; 308(5720):421-4; Klein, et al. Science. 2005 Apr. 15; 308(5720):385-9). This leads to a method of treatment or prevention of the macular degeneration through administration of one of the known complement inhibitors, such as antibodies (antibody fragments, recombinant antibodies, single chain antibodies, humanized and chimeric antibodies) to C3b or a component thereof. An example is Pexelizumab™ (Alexion Pharmaceuticals, Inc., Cheshire, Conn., USA), a humanized, monoclonal, single-chain antibody fragment that inhibits C5, thereby blocking its cleavage into active forms. A potential inhibitor is relatively small, broad-acting C inhibitory protein (termed OmCI), described by Nunn, et al. J Immunol. 2005 Feb. 15; 174(4):2084-91.

Ocular delivery of drug-loaded, sustained-release and optionally targeted nanoparticles by intravitreal administration is a promising route for eye disease because it eliminates the need for multiple injections of drug into the eye. Coupled with the problem of retention of adequate concentrations of therapeutic agent in the pre-corneal area (Mainardes, et al. *Curr Drug Targets* 6, 363-371 (2005)), biodegradable nanoparticles delivered intravitreally have demonstrated localization in the retinal pigment epithelium (Bourges, et al. *Invest Opthalmol Vis Sci* 44, 3562-3569 (2003)) and greater therapeutic efficacy in ocular disease such as autoimmune uveoretinitis (de Kozak, et al. *Eur J Immunol* 34, 3702-3712 (2004)).

In this embodiment, the drug is encapsulated with, and optionally also bound to the microparticles. The preferred size of the microparticles is approximately 100 nm in diameter. The polymer is preferably a polymer such as poly(lactic acid-co-glycolic acid) or polyhydroxyalkanoate which degrades over a period of weeks to months.

In the preferred embodiment, degradable particles less than one micron in diameter, preferably about 100 nm in diameter, are distributed within the eye by subretinal injection or intravitreally injection, where they degrade over a period of from several weeks to several months. In the most preferred case, the microparticles have a high density of adhesive molecules to retinal epithelial cells.

B. Tissue Engineering Matrices and Wound Healing Dressings

The microparticles can be dispersed on or within a tissue engineering matrix for delivery of growth factors or modulatory compounds, as demonstrated in the examples. Many types of materials are known for use in tissue engineering, including materials formed of synthetic polymer, decellularized matrix, collagen, and decellularized tissue. These can be in the form of fibrous matrices or materials such as those used in bone repair or replacement, which consist primarily of materials such as hydroxyapatite. In another embodiment, nanoparticles delivering molecules which are used to enhance wound healing such as antibiotics, growth, angiogenesis stimulating molecules, and other types of drugs, can be applied to wound healing matrices, implants, dressings, bone cements, and other devices which are applied to the site of injury. Preferred antibiotics include vancomycin, ciprofloxacin and anti-infective peptides such as the defensin molecules. In addition, re-vascularization of these grafts can be a problem, hence VEGF, FGF and PDGF could be included in the particles.

The advantage of these particles is that they adhere to the implanted/applied material, where they are retained at the site of injury to provide sustained treatment. Mixtures releasing different amounts or different drugs at different times are particularly advantageous for treatment of wounds such as diabetic wound ulcers. Ligands can be selected to enhance the particles being retained at the site, by binding to extracellular matrix or through non-specific electrostatic binding. In addition, other ligands can be selected to enhance the interaction of particles or matrix with cells that are either added to the material prior to implantation or migrate into the material after implantation.

The following examples describe testing performed using microparticles of the present invention. It should be understood that these examples are not intended to limit the scope, and are provided only to present exemplary embodiments.

EXAMPLE 1

Surface Modification of Biodegradable Polyesters with Fatty Acid Conjugates for Improved Drug Targeting and Modification of Tissue Engineering Materials Materials PLGA with an inherent viscosity of 0.59 dL/g, lot D02022 was supplied from Birmingham Polymers, Inc. Polyvinyl alcohol ($M_w$ average 30-70 Kd), Palmitic acid-N-hydroxysuccinimide ester (NHS-Palmitate), avidin (affinity purified) from egg white and biotin-B-phycoerythrin, biotin immobilized on agarose were all obtained from Sigma Chemical Co. Methylene Chloride and trifluoroethanol were of chromatography grade and supplied by Fischer Chemicals. All other reagents were of reagent grade and used as received.

Preparation of Avidin-palmitic Acid Conjugates

Avidin at 10 mg/ml was reacted with 10-fold excess of NHS-Palmitic acid in PBS containing 2% deoxycholate buffer. The mixture was sonicated briefly and gently mixed at 37° C. for 12 hours. To remove excess fatty acid and hydrolyzed ester, reactants were dialyzed against PBS containing 0.15% deoxycholate. The resultant avidin-palmitate conjugate was verified by reverse-phase HPLC on a Prevail® C18 column with a linear methanol gradient in PBS as the mobile phase and UV detection at 280 nm.

Surface Modification and Characterization:

A modified water-in-oil-in-water (W/O/W) emulsion method was used for preparation of fatty acid PLGA particles. In the first emulsion, fluorescent bovine serum albumin (BSA-FITC) in 100 μL of PBS was added drop wise to a vortexing PLGA solution (5 ml) dissolved in methylene chloride and trifluoroethanol (4:1) % V/V. This first emulsion (W/O) was rapidly added to 200 ml of 5% PVA containing the various concentrations of avidin-palmitic acid investigated. This external phase underwent vigorous stirring for 4 hours at constant room temperature to evaporate methylene chloride and trifluoroethanol. The resultant emulsion was then purified by centrifugation at 12,000 g for 15 minutes then washed 3× with DI water. No subsequent filtration or classification of particles took place in this study. The particles were freeze-dried then stored at −20° C. Samples were characterized by Scanning Electron Microscopy (SEM). Samples were sputter-coated with gold under vacuum in an argon atmosphere using a sputter current of 40 mA (Dynavac Mini Coater, Dynavac USA). SEM analysis was carried out with a Philips XL30 SEM using a LaB electron gun with an accelerating voltage of 5 to 10 kV.

Surface Density and Functional Specificity

A calorimetric assay with 2-Hydroxyazobenzen-4'-Carboxylic Acid (HABA) was used to quantitate the density of surface avidin groups on PLGA particles. HABA binds to avidin to produce a yellow-orange colored complex which absorbs at 500 nm. First, a linear relationship between avidin in solution and HABA absorbance was obtained by measuring the absorbance at 500 nm. This standardized relationship was then used to quantitate the density of surface avidin groups. In this assay 3 mg aliquots of dried particles were suspended in 1 ml of 10 mM HABA (24.2 mg HABA in 10 mM NaOH). Biotin-phycoerythrin (Biotin-PE), a biotin conjugate of the red fluorescent protein (PE) (240 kD), was used to monitor surface functionality. On a rotary shaker the indicated amounts of biotin-PE in PBS were added to 10 mg of plain and surface modified particles. These solutions were incubated for 15 min then centrifuged (10 min/11,000 g) and washed 3× in DI water. Particle fluorescence was measured by flow cytometry.

Affinity to Target Under Dynamic Conditions:

Biotinylated agarose beads (2 ml of 4% crosslinked agarose) were put into a fritted glass column and allowed to settle prior to addition of plain or modified particles. The bed was briefly sonicated to eliminate trapped air bubbles. Particles suspended in PBS were gently added to the top of the packing and allowed to settle into the packed bed prior to elution with PBS. The volume of particles added to the bed did not exceed a tenth of the volume of the packed bed. The column was then carefully filled with buffer and a constant flow of buffer at 0.2 ml/min was maintained by a Jasco pump. Fractions were collected every 0.5 ml into polystyrene UV cuevettes and sample turbidity was analyzed by UV spectrophotometry at 600 nm. Turbidity of the mixture was an indicator of particle elution of the column. For modified particles, when turbidity subsided, a 6M guanidine hydrochloride was added to the column and fractions were collected as described.

Surface Stability and Kinetics of BSA Release:

Release of encapsulated BSA-FITC and surface-bound biotin-PE were carried out in phosphate buffer saline at 37° C. At the indicated time points samples were centrifuged for 10 min at 11,000 g and 1 ml supernatant from the samples was removed and replaced with fresh buffer preincubated at 37° C. The FITC and PE content was measured by fluorescence (($\lambda_{excitation}$=480, $\lambda_{emission}$=520) for BSA-FITC and ($\lambda_{excitation}$=529, $\lambda_{emission}$=576) for biotin-PE. The fraction of protein released was calculated by dividing the amount of BSA-FITC or biotin-PE at the indicated time points by the total content of both proteins in 10 mg of the same stock of particles. Total BSA-FITC content was measured by dissolving 10 mg of particles in 1N NaOH overnight. A standard was prepared by titrating BSA-FITC in 1N NaOH. Since Biotin-PE was localized to the surface of the particles, red fluorescence of an aliquot of (5 mg) particles was measured directly without need for dissolution.

Surface Modification of PLGA Scaffolds:

PLGA 50/50 scaffolds were prepared by a salt-leaching method (25). PLGA was dissolved in methylene chloride (10 mg in 500 ul). Sodium chloride particles (100 mg with an averaged diameter, $100 \leq d \leq 250$) were sprinkled into a round PVDF containers (Cole Parmer #H-08936-00) followed by addition of PLGA solution. After solvent evaporation (24 hthes at room temperature), scaffolds were washed thoroughly in DI water for three days. Scaffolds were freeze dried and stored at −20° C. for later use. Avidin-palmitic acid incorporation was a simple deposition procedure. A 100 ul drop was regionally placed on top of dried scaffolds and allowed to soak in for 15 min at RT, followed by washing 5× in 1×PBS+ 1% BSA. For surface staining, the entire scaffold was incubated in a biotin-PE solution for 10 min at room temperature followed by a second wash in DI water.

Results and Discussion:

Palmitoylation of Avidin

The overall scheme to modify a protein with palmitic acid is shown in FIG. 1A. NHS-palmitic acid is added to avidin at 10× molar excess and reacted in the presence of 2% deoxycholate detergent. The NHS ester reacts with avidin amine groups producing a stable amide linkage and rendering the protein hydrophobic. Both reaction and purification steps were in the presence of detergent to prevent palmitate vesicle formation (Huang J Biol Chem 1980; 255(17):8015-8). Compared to free avidin, which eluted as a single uniform peak with buffer alone, avidin-palmitic acid exhibited some aggregation and eluted with methanol in the mobile phase. This reflects the enhanced hydrophobicity of the conjugate. At higher methanol concentrations in the mobile phase we observed several elution peaks indicating different degrees of conjugate association with the column. A possible explanation is that NHS-palmitic acid targets individual lysine residues as well as the amino terminus of the protein for conjugation; a process that can yield heterogeneous populations of palmitoylated avidin that associate differently with the hydrophobic stationary phase.

Effect of Surface Modification on Particle Morphology

Both plain and palmitoylated avidin particles displayed heterogeneous size distributions. The average diameter of plain and surface modified particles ranged from 4-7 um. Therefore, the presence of avidin-palmitate in the emulsion and at the concentrations used in this study did not impact significantly on the size distribution of the particles. Strikingly, microparticles prepared with conjugate in the emulsion showed a characteristic texture and surface roughness by SEM. This characteristic varied with the concentration of avidin-palmitic acid in the emulsion. These images indicate that palmitic acid in the form of vesicles or lamellae spread onto the surface of the PLGA during formation of the particles. Surface spreading is facilitated by mechanical dispersion or the presence of solvent (methylene chloride and trifluoroethanol during the solvent evaporation step) or the presence of low concentrations of detergent (0.15% deoxycholate) in the final emulsion and during formation of the particles.

The observed characteristic changes in the surface morphology of PLGA upon the addition of lipid or other amphiphilic co-stablizers have been observed previously in similar systems. For example, when 1,2-dipalmitoylphosphatidycholine (DPPC) was used to stabilize PLGA emulsions, significant changes in the surface chemistry were observed by X-ray photoelectron spectroscopy (Evora et al. J Control Release 1998; 51(2-3):143-52). The study is consistent with this observation and supports the fact that the low surface energy of lipid (DPPC) or palmitic acid, in contrast with the high surface energy of PVA, dominates the surface chemistry of PLGA contributing to the observed morphological changes. The study, however, highlights that these changes may also facilitate the presentation of surface functional groups for coupling to proteins.

Surface Density and Functionality of Avidin-palmitic Acid on PLGA Particles

An increase in the absorbance of HABA at 500 nm correlates with the presence of avidin in solution. This relationship was used to verify and quantitate the density of surface avidin groups on PLGA particles (Table 1). An apparent maximum in surface density was observed with 0.25 mg of the conjugate per mg of PLGA in emulsion. The efficiency of avidin-palmitate incorporation into particles ranged between 14 to 24% with higher efficiencies of incorporation observed at lower concentrations of the avidin-palmitate in the emulsion. The presence of an apparent maximum may therefore reflect the natural tendency of the fatty acid to aggregate at higher concentrations; limiting its partitioning into the forming PLGA phase.

To ascertain the functionality and specificity of incorporated avidin to target biotinylated ligand, the fluorescence of plain and modified particles treated with biotin-PE was compared by flow cytometry. The mean channel fluorescence of surface modified particles was approximately three orders of magnitude greater than control microparticles. This functional specificity was also qualitatively confirmed by fluorescence microscopy. Fluorescence images showed regions of brighter fluorescence indicating local high density binding regions on the particles where conjugate might have localized.

Figure 2:
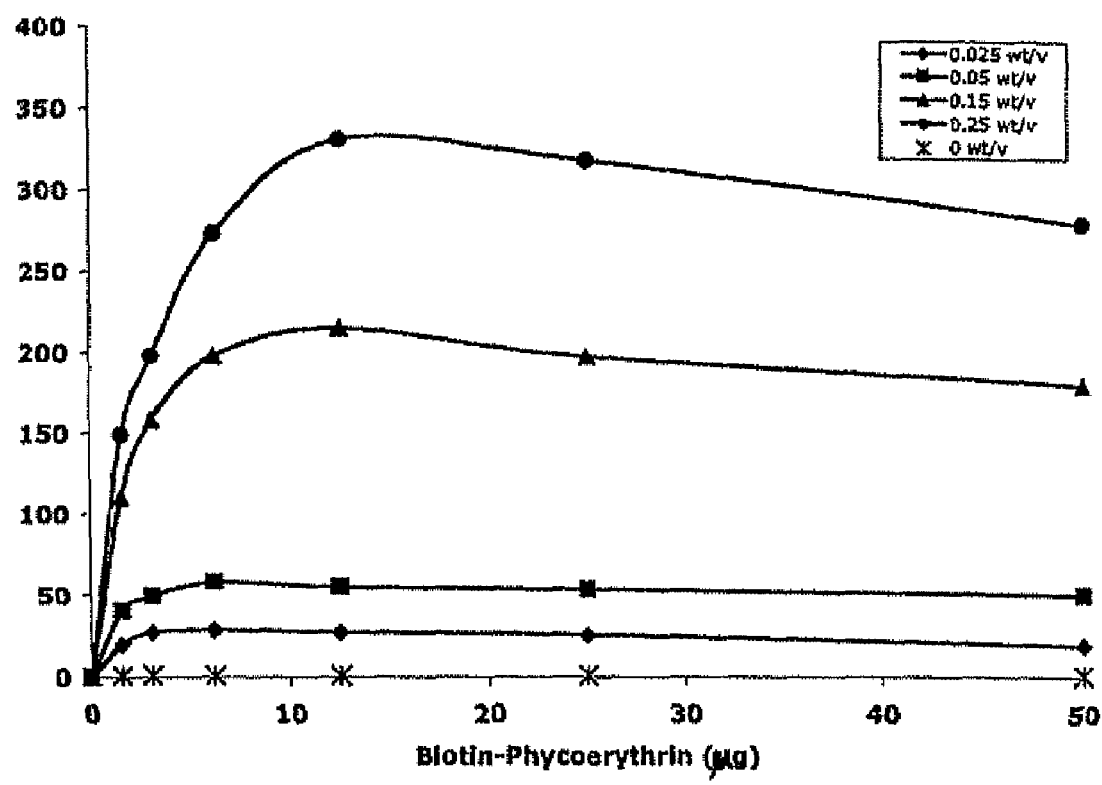

To determine the degree of molecular crowding on the surface of treated particles, biotin-PE was titrated onto microparticles prepared with various concentrations of avidin-palmitic acid (FIG. 2). Surfaces modified with increasing amounts (0, 0.025 wt/v, 0.05 wt/v, 0.15 wt/v, 0.25 wt/v) of the conjugate bound more of the biotinylated fluorophore, as reflected by the higher mean channel fluorescence (MCF). A self-quenching of PE was observed with higher concentrations of biotin-PE added to the particles. Self-quenching which results in a slight decrease in MCF with increasing concentration of fluorophore, occurs with the 'crowding' of fluorophores in localized regions in the proximity of 50-100 Å (Lakowicz J R. Principles of Fluorescence Spectroscopy. New York: Plenum Press; 1986); an indication of the molecular crowding and high density of biotin-PE at the surface of the particles.

Functional Avidity of Surface Modified Microparticles Under Dynamic Conditions

In physiological settings injected particles rarely remain static but undergo a shearing due to flow and encounters with cells and tissue. Critical to the function of surface active particles in these settings is their ability to bind their target (Hammer et al. Annu. Rev. Mater. Res. 2001; 31:387-40). To assess functional avidity under dynamic conditions, plain and surface modified microparticles were injected into a column packed with biotinylated agarose beads followed by elution with saline buffer. Plain microparticles eluted quickly from the column with PBS; modified microparticles, however, visibly adhered to the packing and did not elute even with high buffer flow rates that physically disrupted the packing. Elution of the modified particles required the addition of 6M guandium hydrochloride (GuHCl); a strong protein denaturant known to disrupt the biotin-avidin linkage. A mass balance showed that while 1-3% wt plain microparticles adhered nonspecifically to the column packing after buffer elution, 80-90% of surface modified particles remained associated with the column prior to GuHCl elution.

The Effect of Surface Modification on the Encapsulation Efficiency of BSA

Because the strategy involved the simultaneous encapsulation and surface modification of particles at the emulsion stage, the addition of avidin-palmitic acid might affect the encapsulation efficiency of BSA. Therefore the amount of encapsulated BSA in PLGA particles modified with various concentrations of avidin-palmitate in the emulsion was measured (Table 2).

TABLE 2

| Avidin-Palmitate (wt/vol) | PVA (wt/vol) | Particle Yield % | % Encapsulation (mg BSA/mg Polymer)$_{final}$ / (mg BSA/mg Polymer)$_{initial}$ | Avidin density (ug/mg polymer) | Maximal Biotin-PE Binding (ug/mg polymer) |
|---|---|---|---|---|---|
| 0 | 2.5 | 40 ± 5 | 18.3 ± 2 | N/A | N/A |
| 0.025 | 2.5 | 57 ± 5 | 30.7 ± 2 | 6 ± 1 | 1 |
| 0.05 | 2.5 | 56 ± 7 | 38.1 ± 4 | 9.5 ± 2 | 1.25 |
| 0.15 | 2.5 | 92 ± 6 | 46.0 ± 3 | 30 ± 2 | 2.0 |
| 0.25 | 2.5 | 98 ± 10 | 77.8 ± 5 | 35 ± 3 | 2.5 |

The results indicated that palmitoylation of microparticles enhanced BSA encapsulation in a concentration dependent manner. The encapsulation efficiency of particles modified with 0.25 (wt/vol) avidin-palmitate was four fold greater than unmodified particles. There has been an increase in the yield of particles with higher concentrations of avidin-palmitate in the emulsion (Table 2). Others have found similar effects on the encapsulation efficiency and particle yields with the addition of pegylated Vitamin-E or the lipid DPPC to a PLGA emulsion (Mu et al. J Control Release 2003; 86(1):33-48; Mu et al. J Control Release 2002; 80(1-3):129-44). A possible mechanism for this general effect might involve the increased hydrophobic stabilization due to the presence of co-stabilizing amphipathic molecules such as fatty acids or lipids, facilitating enhancements in PLGA particle formation and encapsulation efficiency (Thomas et al. J Pharm Sci 1998; 87(3): 259-68).

Kinetics of BSA Release and Stability of the Avidin-palmitate Layer

Figure 3:
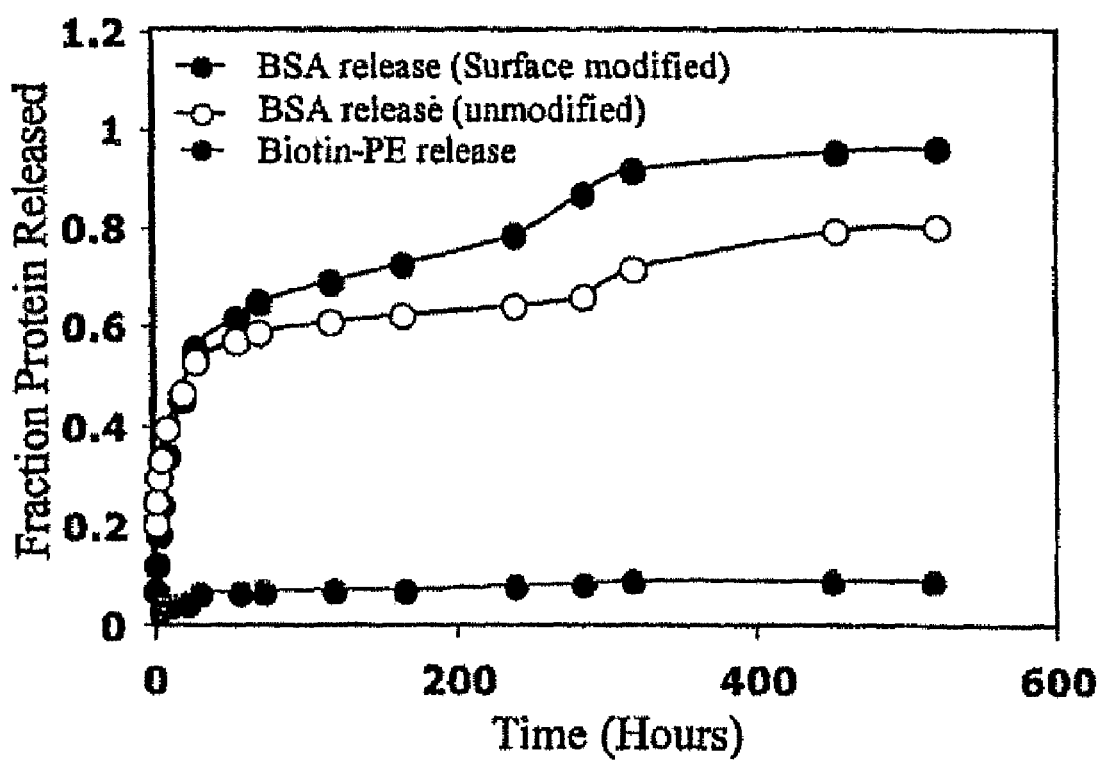

FIG. 3 shows the release profiles of plain and surface modified microparticles over the duration of a controlled release experiment at 37° C. for 25 days. Both plain and modified particles had very similar BSA release kinetics with an initial release burst during the first 24 hours followed by a gradual release and a bulk erosion step (12 days) taking place nearly at the same time for surface modified and unmodified particles. PE fluorescence was almost negligible in the supernatant. Visually, centrifuged particles appeared bright red during the entire time course of the experiment. A cumulative loss of less than 10% PE fluorescence was detected over this period of time indicating stable surface functionality over the time of the experiment.

Using SEM, the morphology of the both plain and modified particles was examined after 21 days. Surprisingly, while plain microparticles showed substantial morphological changes at the endpoint, modified particles were relatively spherical in shape. In addition to showing less drastic morphologic changes by SEM, a distinct capping layer was observed in most microparticles examined. Because of the distinct surface topology associated with surface modification, coupled with persistent binding avidity over the time course these of the experiment, it was hypothesize that the additional surface layer observed in eroded modified microparticles might be due to surface rearrangement of the avidin-palmitic acid groups and reorganization during sphere degradation.

The fact that surface activity (>90%) was persistent for several weeks, coupled with greatly reduced changes in morphology and a possible reorganization of targeting groups during controlled release suggests a significant robustness and resiliency of the palmitoylated avidin surface. This is in light of the observation that the surface likely experiences an acidic microclimate because of polymer hydrolysis (Mader et al. Pharm Res 1998; 15(5):787-93; Brunner et al Pharm Res 1999; 16(6):847-53; Shenderova et al. Pharm Res 1999; 16(2):241-8).

Surface Modification of PLGA Scaffolds:

The approach to surface modification of PLGA particles was translated to an effective strategy for modifying synthetic matrices for tissue engineering applications. Scaffolds regionally treated with avidin-palmitic acid displayed bright red fluorescence, when incubated with biotin-PE, indicative of surface functionality only in those treated regions. Moreover, these scaffolds still maintained their red color after 3 weeks in PBS and 37° C. This approach is simple and facilitates three important aspects for successful tissue growth: 1) The ability of the matrix to be reliably and easily functionalized for selective cell attachment, 2) flexibility in terms of attaching a variety of ligands, and 3) sustained presentation of ligands for long-term proliferation and differentiation of attached cells on the matrix.

A strategy for surface modification of PLGA by introducing a functionally active amphipathic fatty acid, palmitic acid coupled to the ligand of interest (avidin) during the emulsion preparation of PLGA particles. This strategy was also translated to regional modification of PLGA scaffolds for tissue engineering applications. Because of the generality of this system and its flexibility, different ligands may be attached to palmitic acid facilitating surface modification with a variety of ligands and improving upon in vivo particle targeting or clearance. For example combinations of palmitoylated PEG and palmitoylated-avidin incorporated on the same particle may serve as ideal vehicles that combine high circulation lifetime with prolonged targeted drug delivery for in vivo applications. In addition, the combination of regional modification on PLGA scaffolds and ease of adjusting the density and type of ligand make for a powerful strategy to adjusting ratios of different cell types for various applications such as co-culture and growth of functional tissue composed of several cell types (Quirk et al. Biotech. Bioeng. 2003; 81(5):625-628)).

EXAMPLE 2

Non-specific Targeting with LPS for Delivery of a Protein

Lipopolysaccharide, LPS, represents the main outer membrane component of Gram-negative bacteria and plays a key role during severe Gram-negative infection. LPS is recognized by the TOLL-like receptor 4 and is one of a class of ligands called PAMPS (Pathogen Associated Molecular Patterns) which target TOLL receptors associated with innate immunity (Non-specific immunity). These are very effective components of adjuvants that help prime the innate immune response against antigens for vaccination. As a result they are critical components of adjuvants such as complete Freunds adjuvant that stimulate a vigourous immune response. LPS is a polysaccharide backbone with pendant fatty acids.

A. Vaccination by Subcutaneous Administration

In this particular application ovalbumin antigen is encapsulated and mice are vaccinated by subcutaneous administration with particles that have been modified with LPS and the results compared with mice vaccinated with unmodified particles encapsulating the same antigen.

Modified LPS particles induce a powerful response to the ovalbumin antigen, whereas the unmodified particles showed very little response. Blank particles also induced no response.

Methods and Materials.

LPS is added during formation of the microparticles, preferably during emulsion formation, in a ratio of between 1 to 10 mg LPS per 200 mg of polymer. Ovalbumin encapsulation is between 100 µg to 10 mg per 200 mg of polymer during emulsion formation.

Mice were vaccinated subcutaneously with LPS/OVA particles, OVA particles with no LPS and blank particles. Three days later mice were sacrificed and splenocytes isolated. Splenocytes were stimulated with OVA antigen in vitro to check for immune response. If successful vaccination took place splenocytes would respond to OVA antigen in a dose dependent manner. If no vaccination took place splenocytes would not respond.

Results

Figure 4A:
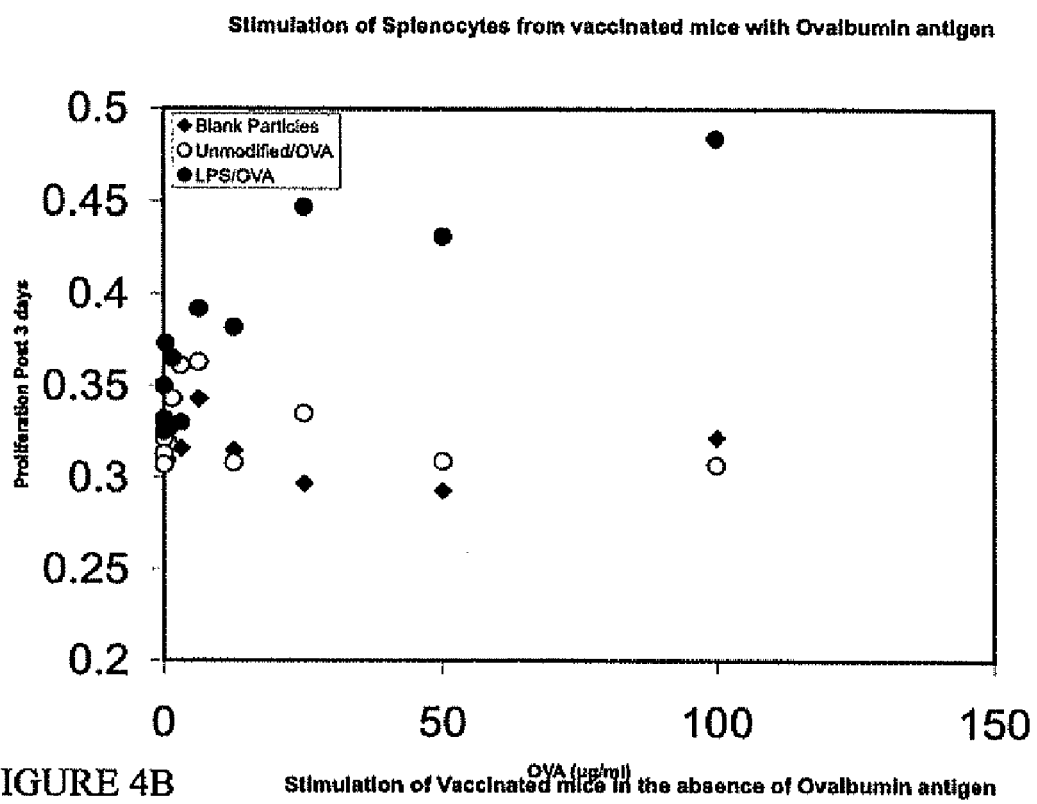
Figure 4B:
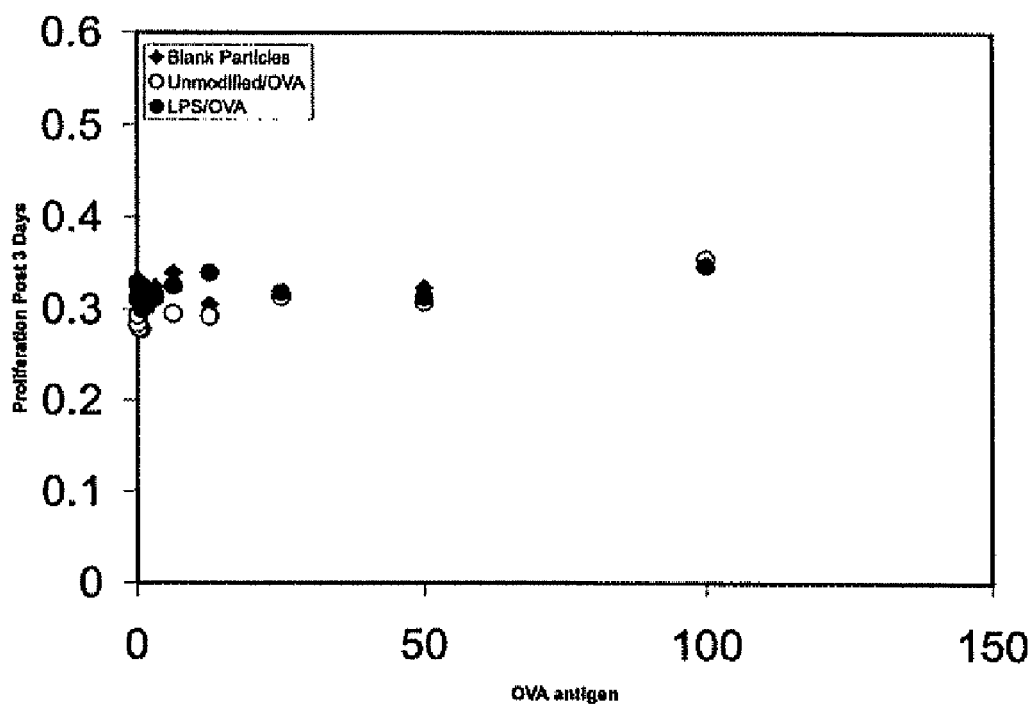

FIGS. 4A and 4B are graphs of the stimulation of splenocytes from mice vaccinated by subcutaneous administration of LPS targeted microparticles encapsulating ovalbumin (closed circles) or with control microparticles: no ovalbumin (closed diamonds), no LPS targeting (open circles). FIG. 4A is stimulation of splenocytes from vaccinated mice; FIG. 4B is stimulation of vaccinated mice in the absence of ovalbumin antigen.

B. Oral Vaccination

Similar results were obtained when particles were administered orally by oral gavage in fasted mice. A good immunization response was observed after two weeks with one single dose of particles fed to fasted mice. No boosters were given. Results are shown in FIGS. 5A and 5B. FIGS. 5A and 5B are graphs of the stimulation of splenocytes from mice vaccinated by oral administration of LPS targeted microparticles encapsulating ovalbumin (closed circles) or with controls: phosphate buffered saline (closed squares), no LPS targeting (open circles). FIG. 5A is stimulation of splenocytes from vaccinated mice; FIG. 5B is stimulation of vaccinated mice in the absence of ovalbumin antigen.

EXAMPLE 3

Enhanced Targeting of Microparticles Through the Use of Star or Branched PEG Linkers An efficient method which facilitates simple attachment of T cell antigens to a macromolecular carrier which encapsulates a high density of immunomodulatory drug was developed. Antigen-presenting drug carriers were constructed from a non-toxic, multi-branched polyethylene glycol/polyamidoamine (PEG/PAMAM) dendritic vehicle. T cell antigens were tethered to the branches of this vehicle while drug was efficiently encapsulated in the core PAMAM which acts as a 'nanoreservoir' of drug. The potency of these vehicles in modulating the T cell response with antibodies and major histocompatability ligands to specific T cell populations was demonstrated. Antigen-presenting carriers encapsulating the antimitogenic drug, doxorubicin bound their target T cells with avidities 10-100 fold greater than free antigen and consistently downregulated the T cell response, while drug-free constructs elicited strong stimulation of the target populations. Owing to the flexibility over the nature and density of antigen presented as well as drug incorporation, these high avidity artificial antigen presenting vehicles have wide clinical use in a dual role as potent immunostimulatory or immunosuppressive tools.

A defining characteristic of the T cell immune response is its exquisite specific recognition of antigen. This specific recognition in T cells is governed by the interaction of clonally distributed T cell receptor (TCRs) with ligands on antigen presenting cells composed of short peptides derived from internalized protein antigen and bound to major histocompatability (MHC) Class I or Class II molecules. Lack of recognition of cells that have been infected by virus, transformed or otherwise altered or faulty recognition of self-antigen can mediate the pathogenesis of malignancies and autoimmune diseases. The T cell receptor complex is therefore an important target for modulation of these disease states.

While the ability to track the intensity and breadth of the antigen-specific T cell response is clearly useful for disease diagnosis, the added ability to target and modulate this response can be used to fix immune system defects and restoring immune competence. One approach for modulating the antigen-specific response involves the induction of antigen-specific T cell unresponsiveness or anergy by exposure to controlled doses of antibodies to antigen-specific T cells or peptide/major histocompatability ligands (peptide/MHC). A second approach involves the conjugation of these reagents to immunosuppressive drugs for direct delivery to target T cells. Conjugation of drug to carrier antigens, however requires indirect and often difficult chemistries to achieve unhindered antigen-presentation coupled with effective drug delivery. Furthermore, the low-affinity of the peptide/MHC-TCR, (1-100 μm) coupled with the fact that most antigen-specific T cell subsets are usually circulating at low numbers has precluded the use of soluble peptide/MHC monomers for sustained interactions to antigen-specific T cells. Thus multimerization of the peptide/MHC is often necessary for enhanced affinities to target T cells. It was hypothesized that T cell targeting could be improved by the use of constructs with multiple T cell antigens, permitting binding to the T cell with enhanced avidity and significantly lower dissociation rates. If such constructs could be produced with the added ability to load drug molecules, they would be attractive reagents for sustaining the interactions necessary for drug delivery to antigen-specific T cells.

Soluble multivalent molecules were combined with a technology that delivers a high density of drug to the cellular target, thereby yielding a versatile, physiologically compatible, multifunctional system that combines high avidity interactions with targeted drug delivery to T cell subsets. A robust, non-toxic, antigen-presenting carrier was engineered by linking poly(ethylene glycol) chains (PEG) to a 'nanoreservoir' poly(amidoamine) spherical core (PAMAM) which functions as a high capacity drug carrier. Doxorubicin was efficiently encapsulated in the PAMAM core (32-mol doxorubicin per mol construct). Biotinylated antibodies or biotinylated MHC were non-covalently attached to the PEG chains via streptavidin linkers that were covalently linked to PEG. Approximately 13 streptavidin molecules were attached per construct. The constructs are specific and bind T cells with an enhanced avidity, 10-100 times greater than free antibodies or peptide/MHC chimeras. The complexes are small, with hydrodynamic diameters in the range of 20-50 nm, allowing efficient internalization and simultaneous fluorescent detection. In vitro experiments with T cell specific antibody, anti-CD3ε, coupled constructs loaded with doxorubicin revealed a potent inhibition of proliferation despite the presence of stimulation. Experiments with peptide-specific MHC similarly revealed a significant modulation of the T cell IL-2 response and end-point proliferation.

Methods and Materials

Mice: Balb/C mice (6-8 weeks) were obtained from Jackson Laboratories (Bar Harbor, Me.). 2C TCR transgenic mice breeding pair were a kind gift from Dr. Fadi Lakkis (Yale University School of Medicine). 2C mice were maintained as heterozygous by breading on a C57BL6 background in the animal facility. Phenotypes were tested with the clonotypic 1B2 antibody, which was provided by Dr. Jonathan Schneck (Johns Hopkins School of Medicine).

Cells: All cells used were obtained from homogenized naive mouse spleens after depletion of RBC by hypotonic lysis. CD8+ cells were isolated by negative selection from 2C splenocytes using CD8+ T cell subset enrichment columns (R&D systems). Purity>95% was routinely obtained.

PEG/PAMAM: PAMAM Generation 6 (Aldrich) 10 wt % in methanol was evaporated under a gentle stream of nitrogen and placed under high vacuum overnight before further manipulation. To prepare fluorescently labeled constructs a 24 fold molar excess of Boc-NH-PEG3400-NHS and a 6 fold molar excess of fluorescein-PEG5000-NHS (Nektar Pharmaceuticals, Huntsville Ala.) were added to PAMAM in a 0.2 M borate buffer pH 8.0. For unlabeled constructs a 30 fold molar excess of PEG3400 was used. The mixture was vortexed gently and placed on a rotary shaker for 24 hours. Unreacted PEG was removed by dialysis in a 10,000 MWCO Slide-a-Lyser (Pierce Chemical, Rockford Ill.) with borate as the dialysis buffer. To remove the tBoc protecting group, the complex was lyophilized for 48 hours and redissolved in trifluoroacetic acid for 30 minutes at room temperature with constant stirring. Trifluoroacetic acid was removed under vacuum for 1 hour. The remaining product was dissolved in borate buffer followed by dialysis in water. The final PEG/PAMAM complex was lyophilized once more and stored at −20° C. The characterization of these complexes is discussed in detail in a previous report[12].

Streptavidin-PEG/PAMAM: Streptavidin (Sigma) was activated for amine coupling by dissolving at 1 mg/ml in 0.1 M MES, 0.5 M NaCl buffer pH 5.1. To form active ester functional groups for coupling NHS and EDC (Pierce Chemical Co.) was added at a concentration of 5 mM and 2 mM respectively and allowed to react for 15 min at room temperature. The unreacted EDC was quenched with 2-mercaptoethaol at a final concentration of 20 mM. For amine coupling to the PEG/PAMAM, a 100 fold molar excess of activated streptavidin was added to the PEG/PAMAM and reacted for 2 hours at room temperature. Excess reactant and unconjugated streptavidin was removed by extensive dialysis in a 200K MWCO CE ester membrane (Spectrum Laboratories, Rancho Domingeuz Calif.). Homogeneity of the complexes was assessed by reverse phase HPLC with 30% acetonitrile as the mobile phase.

Dynamic light scattering: Sizes were measured by dynamic light scattering (DLS). The instrument consisted of a diode pumped laser (Verdi V-2/V-5, Coherent) operating at 532 nm, an ALV-SP S/N 30 goniometer (ALV-GmbH, Langen, Germany) with index matching vat filled with doubly filtered (0.1 mm) toluene, and an ALV-500 correlator. Low concentrations of constructs (<5 ug/mL) were pipetted into a cleaned borosilicate culture tube before measuring the intensity of the auto-correlation function at a 90° scattering angle. The hydrodynamic radius, RH, was determined by non-linear least squares fitting (ALV software) of the resulting second order cumulants.

Antibody and MHC coupling: Biotinylated antibodies (biotin-conjugated hamster anti-mouse CD3ε and biotin-conjugated rat anti mouse CD45R/B220) (BD Biosciences Pharmingen) were used without further purification. Soluble MHC-Ig dimers $L^d$-Ig were provided by Dr. Jonathan Schneck (Johns Hopkins School of Medicine). MHC monomers were prepared from the same dimer stock used in binding experiments by papain treatment of the MHC-Ig and purified as described (Pierce Immunopure Fab preparation kit). Preparation of MHC-Ig Fab fragments by papain treatment yielded functionally active protein that specifically bound TCR immobilized to the surface of a biosensor (Biacore) (data not shown). MHC $L^d$ monomers and dimer were fluorescently labeled with fluorescein isothiocyanate (FITC) (Molecular probes) at pH 7.4 and purified by size exclusion chromatography. Protein concentrations were determined spectrophotometrically by measuring the absorbance at 280 nm. Both $L^d$ monomers and dimers were loaded with peptide by stripping under mild acidic conditions (pH 6.5) and refolded in the presence of 40-fold molar excess peptide and 2-fold molar excess b2-microglobulin. Using a conformationally sensitive ELISA, it was estimated that >85% of the $L^d$ monomers were folded properly. Biotinylated antibodies or $L^d$ monomer were added at a 50 fold molar excess to streptavidin-coupled PEG/PAMAM and incubated overnight at 4° C. followed by dialysis in a 300K MWCO CE membrane (Spectrum Laboratories).

Doxorubicin loading of PEG/PAMAM constructs: Doxorubicin was dissolved in water at a final concentration of 2.5 mg/ml and added to a final concentration of 100 nM to PEG/PAMAM constructs in PBS pH 7.4. The solution was mixed gently for 2 hours at 37° C. then 24 hours at 4° C., followed by dialysis in 7000 MWCO membranes (Pierce Chemical). Encapsulation efficiency was assessed by fluorescence emission at 570 nm with 488 nm excitation. The amount of doxorubicin loaded was deduced from a doxorubicin calibration standard. To assess the magnitude of doxorubicin fluorescence enhancement in the presence of PEG/PAMAM constructs, doxorubicin at 2.5 mg/ml in water was titrated in 0.1 uL volumes in a fluorometer cuevette in the presence or absence of PEG/PAMAM constructs. Difference spectra were collected in the range 500-600 nm with excitation at 488 nm.

In Vitro proliferation assays: Cells were adjusted to a concentration of $1 \times 10^7$ cells/ml in complete media. Plates were coated with various concentrations of anti-CD3ε antibodies according to established protocols. $2 \times 10^5$ cells were plated per well. Cells were treated with 20 nM complexes either loaded or unloaded with doxorubicin and incubated at 37° C., 5% $CO_2$. To analyze the kinetics of IL-2 production, supernatants at the indicated time points were harvested and analyzed by ELISA for IL-2 according to manufacturer's instructions (BD Biosciences, San Diego, Calif.). On Day 3 T cell proliferation was analyzed with a colorimetric assay for quantification of cell proliferation and viability, WST-1, according to manufacturers protocol (Roche Diagnostics GmbH, Pennsburg, Germany).

T cell Binding Assay: $1 \times 10^5$ cells were incubated with varying concentrations of the reagents discussed constructs until equilibrium binding was reached (2 hrs, 4° C.). Cells were washed 3× with PBS with 1% Fetal bovine Serum and 0.1% Sodium azide and analyzed by flow cytometry. The mean channel fluorescence (MCF) was a measure of the amount of reagent bound. Specific binding was normalized to the maximum mean channel fluorescence.

FRET measurements: PEG/PAMAM constructs at 5 mg/ml were labeled with a final concentration of 2.5 uM Alex Fluor® dye 546 (Donor) or Alex Fluor® 568 (Acceptor) (Molecular Probes, Eugene, Oreg.) or equimolar mixtures of both fluorophores in a carbonate buffer pH 8.3. After removal of excess dye by dialysis the complexes were excited at 540 nm and emission spectra were collected in the range (550-650 nm). Energy transfer efficiency, E, was calculated from the relative fluorescence yield in the presence ($F_{da}$) and absence of acceptor ($F_d$)[43,44] and was used to calculate the energy transfer distance R from:

$$1 - \left(\frac{F_{da}}{F_d}\right) = \frac{R_0^6}{R_0^6 + R^6} \text{ where } R_0 = 7.0 \text{ nm}$$

Results

A branched, biocompatible, (24-30 arm) artificial antigen-presenting polymer was constructed from polyethylene glycol and generation 6 (G6) polyamidoamine dendrimer (PEG-PAMAM) by methods reported by Luo, Macromolecules 35, 3456-3462 (2002). PAMAM Starburst dendrimers are unique synthetic macromolecules with a branched tree-like structure (Tomalia, et al. *Angewandte Chemie-International Edition in English* 29, 138-175 (1990); Naylor, et al. *Journal of the American Chemical Society* 111, 2339-2341 (1989)). G6 PAMAM tendrils radiate out from a central hydrophobic core to create a well-defined globular architecture with 128 functional amine groups at the surface. Heterobifunctional PEG $M_w$3400 with a protected amine end (HOOC-PEG3400-NH-tBoc) was covalently attached to the PAMAM tendrils and the amine end deprotected after attachment. The working construct was a polymer with radiating amine terminated PEG chains (4.2 nm) linked to a hydrophobic core (6.7 nm). To facilitate detection of the constructs, fluorescein terminated PEG chains were covalently coupled to the dendrimer core at the molar ratio of 1:5 with respect to amine-terminated PEG chains. The PAMAM cores of the constructs can function as drug reservoirs, ideally suited as vehicles for small drugs (Liu, et al. *Abstracts of Papers of the American Chemical Society* 216, U875-U875 (1998); Kono, et al. *Abstracts of Papers of the American Chemical Society* 221, U377-U377 (2001); Jansen, et al. *Journal of the American Chemical Society* 117, 4417-4418 (1995); Jansen, et al. *Science* 266, 1226-1229 (1994)), paramagnetic molecules for contrast enhancement in magnetic resonance imaging (Kobayashi, et al. *Mol Imaging* 2, 1-10 (2003)), oligonucleotides (Yoo, et al. *Pharm Res* 16, 1799-804 (1999)), transgenes (Kobayashi, H. et al. *Bioconjug Chem* 10, 103-11 (1999)) and radionuclides (Kobayashi, *Bioconjug Chem* 10, 103-11 (1999)). Because the magnitude of spatial flexibility of the PEG chains on the construct determines the degree of steric constraint of proteins attached to the amine ends of PEG, the spatial flexibility of branched PEGs was assessed by resonance energy transfer. The amine reactive donor dye, Alexa fluor 546® (Molecular Probes) and an acceptor dye, Alexa Fluor 568®, were conjugated to the amine ends of the unlabeled constructs followed by purification of the construct by dialysis. The distance at which fluorescence energy transfer from the donor dye to acceptor dye is 50% ($R_o$ is 7.0 nm) (Molecular Probes). Saturating concentrations of a 1:1 molar ratio of both dyes conjugated to the construct resulted in a pronounced decrease in donor fluorescence and a sensitization of acceptor fluorescence. The transfer efficiency calculated from the relative fluorescence yields of the donor in the presence and absence of acceptor was between 50 and 57%. This efficiency was used to estimate a proximity distance between the dyes of 6±1 nm. This is sufficient distance for coupling of proteins in the size range of streptavidin (3-4 nm). Streptavidin coupling facilitates the attachment of a wide variety of biotinylated ligands. In addition, because the T cell ligands used in this study were biotinylated with a 2.2 nm biotin spacer arm (NHS-LC-biotin®) Pierce Chemicals, it was estimated there were sufficient flexible spatial interactions between streptavidin coupled T cell ligands and their target receptors on T cells. Analysis of the constructs is consistent with this estimate: the coupling efficiency was approximately 13 streptavidin molecules per construct with 5-10 fluorescein-terminated pendant chains.

The homogeneity of construct was verified by reverse phase HPLC, which revealed a narrow distribution of the PEG/PAMAM and a slightly wider distribution for streptavidin-PEG/PAMAM (SA-PEG/PAMAM) constructs. The SA-PEG/PAMAM eluted earlier on a C18 column, probably due to the decrease in hydrophobicity and increase in molecular size of construct that occurred with streptavidin conjugation. Sizes of the constructs were also measured by dynamic light scattering and estimated at 17.1 nm and 26.4 nm for PEG/PAMAM and SA-PEG/PAMAM respectively.

Antigen-presenting constructs bind their targets with specificity and high avidity: To evaluate the specificity of SA-PEG/PAMAM as a multivalent scaffold for T cell ligands, SA-PEG/PAMAM was coupled to biotinylated antibodies that recognize the T cell CD3 complex and anti-B220 that recognize the CD45R antigen on B cells (negative control). Purified multivalent complexes were incubated at saturating doses with a T cell enriched (B cell depleted) population of splenocytes from Balb/C mice at 4° C. for 2 hrs. The cells were then washed and the bound complexes were analyzed by flow cytometry. Virtually no binding of the control anti-B220 complexes was seen at the saturating dose used in this study, but the specific anti-CD3 complex bound strongly at the same dose. When the anti-CD3 complexes were incubated at various concentrations with T cells, there was a striking enhancement in the binding avidity of the constructs in comparison with native fluorescently labeled anti-CD3 antibody. Because avidity increases with increased valency of binding, and because the PEG/PAMAM constructs have a higher valence (>13) than antibodies, more of the anti-CD3 complexes bound compared to the native antibody at a fixed ligand concentration. These multivalent constructs therefore afford a higher sensitivity of T cell detection at lower concentrations of the reagent.

Because the affinity of peptide/MHC-T cell interactions is lower than antigen-antibody interactions, the efficacy of SA-PEG/PAMAM complexes in increasing the sensitivity of detection of clonotypic antigen-specific T cells was evaluated in a similar binding assay. Biotinylated MHC Class I was coupled the constructs and their binding compared with dimeric MHC constructs to purified murine CD8+ T cell populations. The model system used was a murine alloreactive Class I restricted CD8+ 2C T cell system that recognizes the self-derived mitochondrial peptide, QLSPFPFDL (QL9) presented in the context of the alloantigen Class I MHC H-2L$^d$, ($^{Ql9}$L$^d$) (Sykulev, Y. et al. *Proc Natl Acad Sci USA* 91, 11487-91 (1994)), and has little or no affinity to the same MHC loaded with the negative control peptide YPHFMPNTL (MCMV), ($^{MCMV}$L$^d$). Monomeric H-2L$^d$ was biotinylated at the amine terminus and exogenously loaded with peptides QL9 and MCMV using methods discussed in Fahmy, *Immunity* 14, 135-43 (2001)). Modifications to the MHC similar to those discussed here have been shown to have little or no affect on the MHC-T cell receptor interaction by in vitro biosensor assays (Fahmy, et al. *Immunity* 14, 135-43 (2001)). Similar to binding profiles observed with anti-CD3 constructs, $^{QL9}L^d$ constructs bound 2C T cells with enhanced avidity. The enhanced avidity was two orders of magnitude greater, at half-maximal dose, in comparison with dimeric forms of the MHC ($^{QL9}L^d$-Ig) (Schneck, *Immunol Invest* 29, 163-9 (2000)).

It was hypothesized that the enhanced avidity of these complexes when coupled with the potential capacity of PAMAM for carrying drug would be a powerful means of drug delivery to specific T cell populations. To test this hypothesis, the ability of the constructs to encapsulate the antimitogenic drug doxorubicin was first assessed.

High-density encapsulation of doxorubicin by the PAMAM dendritic core of antigen-presenting constructs. Previous work has shown that doxorubicin (Dox), an anthracycline which intercalates into DNA, can exhibit anti-proliferative effects and induce growth arrest and apoptosis in proliferating T cells. Dox is intrinsically fluorescent, thus detection of the drug is facilitated by fluorescent detection with excitation at 488 nm and peak emission at 570 nm in aqueous solutions. Dox is a weakly basic drug (pKa=7.6) with limited solubility in aqueous environments. Motivated by the potential utility of the hydrophobic dendrimer core as a drug carrier, and the preferential association of Dox with hydrophobic microenvironments (Dox octanol/water partition coefficient is 2), the capacity of the constructs for passive loading of doxorubicin was examined. Constructs were incubated with a 10 fold molar excess of Dox at 4° C. for 24 hours followed by extensive dialysis in 7000 MWCO followed by fluorescence measurements of the complexes. Using a doxorubicin fluorescence calibration standard, it was estimated that approximately 55±10 moles of Dox associated with each mole of construct. To verify that the associated Dox is encapsulated in the dendrimer core it was noted that Dox in an organic-aqueous solution simulating the microenvironment of the PEG/PAMAM constructs showed an enhancement in fluorescence. This enhancement in fluorescence was used to assess the magnitude of Dox association with SA-PEG/PAMAM. A similar enhancement was observed when comparing Dox fluorescence in phosphate buffered saline in the presence of the construct. Since PAMAM constitutes the largest hydrophobic fraction of the complex, the data indicated an association of Dox with SA-PEG/PAMAM similar to associations in organic-aqueous media. The magnitude of this association based on fluorescence enhancement assays was used to deduce the number of moles of associated drug per mole of construct. The data peaked at a maximum lower than the amount deduced from earlier equilibrium measurements. This might have been duo to formation of doxorubicin aggregates in the dialysis chamber contributing to an overestimate of the amount associated with the construct.

The data indicate that Dox is efficiently encapsulated in the dendritic core of the antigen-presenting constructs. Doxorubicin is efficiently released from the dendritic core at low pH. Because drug loaded constructs are small (<100 nm); they are efficiently internalized by their targets. To examine the level of association of Dox with constructs in the acidic microenvironment of endocytic vesicles, drug-construct interactions at pH 5 were monitored. Dox loaded avidin-coupled constructs were immobilized on a biotinylated agarose column, and washed with phosphate buffer saline pH 7.4 before exposure to a low buffer environment simulating lysosomal pH. Upon lowering the pH of the column, a striking increase in Dox concentration in the eluent as monitored by the red fluorescence of the drug was observed. A mass balance revealed that greater than 90% of the Dox was efficiently released from the constructs on lowering the pH of the mobile phase. The data is consistent with a phenomenon known as the 'ion trapping hypothesis', wherein weak bases with a hydrophobic character such as doxorubicin become increasingly charged with lower pH and preferentially partition to acidic compartments. All experiments in the subsequent studies were performed with constructs saturated with doxorubicin at the estimated amount of 32 mol Dox/mol construct.

To test the efficacy of Dox-loaded anti-CD3 constructs in downregulating the proliferative response of T cells in culture, murine Balb/C splenocytes were stimulated with varying doses of plate-bound anti-CD3 in the presence and absence of Dox-loaded anti-CD3 and Dox-loaded anti-B220 constructs (negative control) and measured T cell proliferation after 3 days. In contrast to anti-B220-dox constructs, which showed little or no effect on proliferating T cells, anti-CD3 Dox constructs were potent inhibitors of proliferation. In these experiments, proliferation was affected by two competing mechanisms: An enhancement in proliferation due to the additional stimulus provided by the presentation of anti-CD3-constructs and an inhibition in proliferation due to specific drug delivery to target T cells.

To examine the utility of drug loaded antigen presenting constructs in modulating the response and proliferation of alloreactive antigen-specific T cell subsets, $^{QL9}L^d$-constructs loaded with Dox ($^{Q19}L^d$Dox) and $^{MCMV}L^d$Dox (negative control) were incubated with a purified naive population of cytotoxic T cells, CD8+ T cells, from 2C mouse splenocytes. T cells were stimulated for 3 days in culture in anti-CD3 coated plates in the presence or absence of constructs. To monitor the response of the antigen-specific T cell culture, the amount of IL-2 produced during the first three days of culture and the total T cell proliferation after day 3 was measured, IL-2 is an autocrine cytokine required for growth stimulation and proliferation of T cells and is thus an important indicator of the progression of T cell stimulation. The relative difference in IL-2 production between $^{MCMV}L^d$Dox or $^{Q19}L^d$Dox after day 1 was small and comparable to the amount of IL-2 produced by untreated cells. This is an expected finding since naive T cells require at least 20 hours of sustained signaling to be committed to a vigorous proliferative response. We noticed a discernable change between specific and non-specific inhibition of IL-2 after day 2. At day 3 we observed a marked inhibition in IL-2 release from cells treated with $^{Q19}L^d$Dox relative to untreated cells or cells treated with $^{MCMV}L^d$Dox. The finding that $^{MCMV}Ld^{DOX}$ showed an inhibition effect relative to untreated cells is consistent with the fact that the MCMV peptide in the context of H-$21^d$ is not entirely non-specific to purified 2C T cells in in vitro assays of T cell function.

At low concentrations of plate-bound anti-CD3 and in the absence of Dox-loaded constructs, T cells exhibited a pronounced release of IL-2 and concomitant proliferation which decreased rapidly with higher levels of stimulation. While $^{MCMV}L^d$Dox IL-2 release and proliferation profiles were lower than untreated cells, probably due to non-specific interactions with T cells, it was found that by comparison $^{Q19}L^d$Dox profoundly inhibited the production of IL-2 and the proliferative capacity of antigen-specific T cells by greater than 60%. Furthermore, $^{Q19}L^d$Dox inhibition of IL-2 release was effective over the entire dose range examined. Together these results demonstrate an ability to selectively inhibit the proliferation of polyclonal as well as antigen-specific populations of T cells.

Discussion

The goal was to design a multifunctional system, which can facilitate tracking via high avidity interactions as well as delivering drugs to specific population of T cells. Because of the functionality and demonstrated utility of PAMAM dendrimers as non-toxic, nanoscopic polymers in drug delivery, these polymers were chosen as a starting point and a core for the design of multifunctional antigen presenting constructs. Polyethylene glycol (PEG) was tethered to the dendrimer core for two reasons: First, PEG is a linear polymer which imparts a flexibility to proteins attached to the construct and allows for attached proteins to scan a few nanometers of surface area for attachment to cell surface receptors. Studies with MHC immobilized on planar membranes demonstrated that T cells bound and responded most efficiently when individual MHC molecules were less than 20 nm apart. Second, proteins attached to PEG take on unusual properties such as enhanced solubility, biocompatibility, lower immunogenicity and desirable pharmacokinetics while the main biological functions such as receptor recognition can often be maintained. These are critical properties for long-term use of this technology and eventual utility in clinical settings.

To accommodate the attachment of a wide variety of expensive and difficult to prepare ligands, streptavidin was attached to the PEG chains as an intermediate coupling protein. Streptavidin facilitates the coupling of smaller amounts of biotinylated reagent and expands the application of the scaffold to a wide range of targets. This range of usage with biotinylated reagents that target whole T cell populations or antigen-specific T cell populations was demonstrated. Although the antigen-specific T cell studies in this report have been performed with a class I MHC protein in an alloreactive setting, the system described could be used in conjunction with any biotinylated MHC applicable to other model systems.

Unlike protein-based delivery systems which must be prepared de novo and which have a limited capacity for carrying drug, the PEG/PAMAM complexes described here have the capacity to carry up to 32 mol of doxorubicin per mol of construct. Thus this system offers a therapeutic potential at lower concentrations comparable to dose-dense free drug therapy. Control over the construct size, number of sites available for conjugation and reactivity of the various sites allows for control over the presentation of mixtures of peptide/MHC and auxiliary ligands. The technology discussed is unique because of this versatility. This feature is important for addressing specific issues that depend on the nature and density of ligand presented such as T cell tolerance, which is affected by the density of antigen presented and co-stimulation.

EXAMPLE 4

Attachment of poly(lactide-co-glycolide) (PLGA) Microparticles to Decellularized Scaffolds for Drug Delivery in Cardiovascular Tissue Engineering The use of decellularized scaffolds in cardiovascular tissue engineering is common due to their similar biomechanical properties to native tissue. Unfortunately, these matrices undergo accelerated calcification. The phosphoprotein, osteopontin, inhibits calcification and could be used to decrease mineralization through microparticle delivery. Furthermore, because cardiovascular tissue calcifies in a known geometry, it would be of significant utility if osteopontin could be delivered to specific locations of a matrix.

Methods:

Osteopontin microparticles (125 μg OPN/g PLGA) were produced by spontaneous emulsification, washed by centrifugation, and lyophilized for 24 hours. Sections of a porcine heart valve were harvested, chemically decellularized, and subcutaneously implanted in mice (n=3). One section was co-implanted with osteopontin microparticles, while another was implanted alone as a control. After 7 days the tissue was resected and evaluated for calcification by atomic absorption spectroscopy. In a separate experiment, to demonstrate microparticle attachment, decellularized bovine metatarsal artery was biotinylated and then incubated with avidin coated PLGA microparticles.

Results:

The tissue treated with osteopontin microparticles showed a 45.1% decrease in calcification as compared to untreated tissue. PLGA microparticles were successfully attached to the fibers of a decellularized bovine scaffold.

Conclusions:

These results demonstrate that osteopontin microparticles can help inhibit calcification of cardiovascular structures during/after surgical replacement procedures and can be locally attached for matrix delivery. These particles can work on other types of biological vascular grafts as well (i.e. xenografts for heart valve replacement).

EXAMPLE 5

Nanoparticles for Delivery of Rapamycin to Prevent Restenosis

Rapamycin is currently used to prevent restenosis by application in a polymeric reservoir or coating as part of a stent. The limitations of these devices are avoided through the separate application of the nanoparticles at the time of or immediately after a procedure such as angioplasty, vessel grafting, synthetic vessel implants, synthetic joint implants or other medical implants or at the time of bypass surgery. It has been demonstrated that the short-term application of rapamycin, at the time of implantation, can have significant long-term effects on restenosis. The advantage of the nanoparticles is that there is no systemic delivery, and release of an effective anti-proliferative amount can be achieved over a period of weeks, during the time period most critical for treatment.

A common form of bypass surgery involves resecting the saphenous vein from the leg for autotransplantation to the coronary artery. In 50% of the cases these grafts fail within 5 years—largely due to restenosis. Nanoparticles can be used for the local and sustained delivery of rapamycin, or other anti-proliferative agent to the autologous graft. After resection of the saphenous vein the tissue can be, and often is for an hour or more, suspended in saline while the patient's chest is opened for graft implantation. The nanoparticles can be administered at this time. One hour of particle attachment time in saline would be more than sufficient.

Preparation Avidin Coated Rapamycin Nanospheres

Avidin at 10 mg/ml was reacted with 10-fold excess of NHS-Palmitic acid in PBS containing 2% deoxycholate buffer. The mixture was sonicated briefly and gently mixed at 37° C. for 12 hours. To remove excess fatty acid and hydrolyzed ester, reactants were dialyzed against PBS containing 0.15% deoxycholate.

A modified double emulsion method was used for preparation of fatty acid PLGA particles. In this procedure, 1 mg of rhodamine B in 100 μL of PBS, was added drop wise to a vortexing PLGA solution (100 mg PLGA in 2 ml MeCl$_2$). This mixture was then sonicated on ice three times in 10-second intervals. At this point, 4 ml's of and avidin-palmitate/PVA mixture (2 ml avidin-palmitate in 2 ml of 5% PVA) were slowly added to the PLGA solution. This was then sonicated on ice three times in 10-second intervals. After sonication the material was added drop-wise to a stirring 100 ml's of 0.3% PVA. This underwent vigorous stirring for 4 hours at constant room temperature to evaporate methylene chloride. The resultant emulsion was then purified by centrifugation at 12,000 g for 15 minutes then washed 3× with DI water. The particles were freeze-dried then stored at −20° C. Samples were characterized by Scanning Electron Microscopy (SEM). Samples were sputter-coated with gold under vacuum in an argon atmosphere using a sputter current of 40 mA (Dynavac Mini Coater, Dynavac USA). SEM analysis was carried out with a Philips XL30 SEM using a LaB electron gun with an accelerating voltage of 5 to 10 kV.

Attachment of Nanoparticles to Ovine Carotid Artery.

Three 1×1 cm pieces of carotid arteries from sheep were incubated in PLGA avidin labeled nanospheres loaded with rhodamine (as a marker which is predictive of rapamycin encapsulation and release). prepared as described above. The incubation was done in a hybridization oven at 25° C., facilitating attachment of the nanospheres through agitation by placing them in a vial and suspending the vial to a vertically rotating carousel.

A fluorescent micrograph at 10× magnification of untreated sheep carotid artery not incubated in avidin microparticles was compared with a fluorescent micrograph at 10× magnification of treated sheep carotid artery incubated in avidin microparticles. As clearly visible in the micrograph there is a high degree of fluorescene in the treated tissue as compared to the untreated tissue-indicative of rhodamine nanosphere attachment.

Stability of Attachment in a Sheer Stress Environment

A tubular portion of ovine artery was nanosphere coated. After nanosphere attachment the tube was connected to a bioreactor where it supported phosphate buffered saline ("PBS") flow for one hour. After this time, the tissue was removed from the bioreactor, placed in an Eppendorf tube and incubated in fresh PBS to measure the amount of rhodamine released from the conduit. After 1 hour the conduit was placed in a new tube with fresh PBS and the old PBS was measured for fluorescence. Four fractions were measured in this manner. This demonstrated that the nanosphere coated conduit was capable of delivering drug in a controlled fashion without total washout of the particles after sheer stress.

Choice of Particle Size.

Nanoparticles (50-500 nm) were used in the coupling system. Maximizing the surface area to unit mass of particle should improve the binding of the particles to the vascular tissue. Nanoparticles are also better in that washout of the particles will cause downstream occlusion of smaller vessels (capillaries can be as small as 5 microns).

Rapmycin Encapsulation.

Rapamycin was encapsulated in PLGA nanoparticles and bioactivity verified using a PBMC assay. Briefly, PBMC cells were stimulated with IL12 and IL18. In the presence of rapamycin, interferon secretion is inhibited, resulting in an inverse correlation between rapamycin concentration and interferon levels. In this particular experiment, 10 mgs of rapamycin particles were suspended in 10 mls of PBS. At various time points, 100 µl of PBS were taken from the 10 mls for subsequent treatment of the PBMCs. This data indicates that the rapamycin released from the nanoparticles are bioactive.

Rapamycin Dosing.

The desired dosing of rapamycin to autografts based on stent data has been calculated as a target coating amount of rapamycin of between one and 500 µg/mm$^2$, more preferably between 200 µg/mm$^2$ graft and 2 mg/mm$^2$ graft, with approximately 75% of rapamycin eluted at 28 days. Release can occur over a range in dosage from the time of implantation to between three days and six months after implantation.

EXAMPLE 6

Microparticles for Delivery of Antibiotics in Tissue Engineered Matrices, INTEGRA™

Materials and Methods

Integra™, a tissue engineering product used to treat burns as a synthetic skin, was treated with nanoparticles that were designed to adhere to the tissue-like matrix. Three 1×1 cm pieces of INTEGRA™ from were incubated in PLGA avidin labeled nanospheres loaded with rhodamine (as a marker which is predictive of rapamycin encapsulation and release), prepared as described above in Example 5. The incubation was done in a hybridization oven at 25° C., facilitating attachment of the nanospheres through agitation by placing them in a vial and suspending the vial to a vertically rotating carousel.

Results

A fluorescent micrograph at 10× magnification of untreated INTEGRA™ not incubated in avidin microparticles was compared with a fluorescent micrograph at 10× magnification of treated INTEGRA™ incubated in avidin microparticles. As clearly visible in the micrograph there is a high degree of fluorescence in the treated tissue as compared to the untreated tissue-indicative of rhodamine nanosphere attachment.

INTEGRA™ is used as a skin graft for burn victims. Typically, a patient with second or third degree burns is treated with INTEGRA™ for a couple of weeks before an autologous skin graft is applied. Unfortunately, infection is a major problem with this type of treatment. This study demonstrates that the particles can be used to 'dip-coat' INTEGRA™ in nanoparticles such that those nanoparticles attach and deliver agent to the INTEGRA™ for a couple of weeks following application to the wound.

We claim:

1. A tissue engineering matrix, wound dressing, or medical implant comprising polymeric microparticles or nanoparticles for delivery of a therapeutic, nutritional, diagnostic or prophylactic agent incorporated on or within the microparticles or nanoparticles,
   wherein the microparticles or nanoparticles are formed of a polymer having ligands present in a density of between about 1,000 and 10,000,000 ligands per square micron of microparticle or nanoparticle surface area,
   wherein the ligands are inserted into or attached onto the surface of the polymeric microparticles or nanoparticles.

2. The tissue engineering matrix, wound dressing, or medical implant of claim 1 wherein the ligands have a first end incorporated into or attached onto the surface of the polymeric microparticles or nanoparticles and a second end facing outwardly from the surface of the polymeric microparticles or nanoparticles.

3. The matrix of claim 1 wherein the microparticles comprise ligands having bound thereto targeting or attachment molecules.

4. A method of making a tissue engineering matrix, wound dressing, or medical implant comprising forming a tissue engineering matrix, wound dressing, or medical implant comprising microparticles for delivery of a therapeutic, nutritional, diagnostic or prophylactic agent, wherein the microparticles or nanoparticles are formed of polymer having ligands present in a density of between about 1,000 and 10,000,000 ligands per square micron of microparticle or nanoparticle surface area, wherein the ligands are inserted into or attached onto the surface of the polymeric microparticles or nanoparticles.

5. The method of claim 4 wherein the microparticles comprise ligands having a first end incorporated into the surface of the microparticle and a second end facing outwardly from the surface of the microparticle, the ligands being present on the surface of the microparticle and being bound to an agent to be delivered selected from the group consisting of therapeutic, nutritional, diagnostic and prophylactic agents, targeting and attachment molecules.

6. The method of claim 4 comprising administering the tissue engineering matrix, wound dressing or medical implant at the time of or immediately following angioplasty, vessel grafting, tissue or organ transplantation, synthetic vessel implants, synthetic joint implants or other medical implants.

7. The method of claim 4 wherein the microparticles comprise ligands having bound thereto targeting or attachment molecules.

8. The tissue engineering matrix, wound dressing, or medical implant of claim 2, wherein the polymer is a hydrophobic polymer and the ligands are materials with a hydrophile-lipophile balance (HLB) of less than 10, which insert into the surface of the microparticles or nanoparticles.

9. The tissue engineering matrix, wound dressing, or medical implant of claim 8 wherein the nanoparticles or microparticles comprise a hydrophobic polymer having fatty acid conjugates inserted therein and extending outwardly from the polymeric surface.

10. The tissue engineering matrix, wound dressing, or medical implant of claim 1 wherein the ligands are, or are bound to, an agent to be delivered selected from the group consisting of therapeutic agents, nutritional agents, diagnostic agents, prophylactic agents, attachment molecules, targeting molecules, and mixtures thereof.

11. The tissue engineering matrix, wound dressing, or medical implant of claim 10, wherein the nanoparticles or microparticles have bound thereto targeting molecules.

12. The tissue engineering matrix, wound dressing, or medical implant of claim 10, wherein the nanoparticles or microparticles further comprise the agents encapsulated within the polymer.

13. The tissue engineering matrix, wound dressing, or medical implant of claim 12, wherein the nanoparticles or microparticles are formulated for delivery of the same or different agents in the form of a two phase delivery or pulsed delivery.

14. The tissue engineering matrix, wound dressing, or medical implant of claim 1, wherein targeting molecules are bound to the surface of the nanoparticles or microparticles or to the ligands.

15. The tissue engineering matrix, wound dressing, or medical implant of claim 14, wherein the targeting molecules are selected from the group consisting of antibodies, sugars, peptides, and ligands for cell surface receptors.

16. The tissue engineering matrix, wound dressing, or medical implant of claim 10, wherein the ligands are, or are bound to, attachment molecules.

17. The tissue engineering matrix, wound dressing, or medical implant of claim 16, wherein the attachment molecule is selected from the group consisting of strepavidin, avidin, and biotin.

18. The tissue engineering matrix, wound dressing, or medical implant of claim 1, wherein nanoparticles or microparticles further comprise linkers, wherein the linkers are branched and multiple agents to be delivered or attachment molecules are attached via the linkers to each of the ligands.

19. The tissue engineering matrix, wound dressing, or medical implant of claim 1 wherein the agent to be delivered is a cytotoxic or antiproliferative agent.

* * * * *